US011707725B2

(12) United States Patent
Baek et al.

(10) Patent No.: US 11,707,725 B2
(45) Date of Patent: Jul. 25, 2023

(54) ACID GAS ABSORBENT IN BIOGAS AND BIOGAS PURIFICATION SYSTEM USING THE SAME

(71) Applicant: KOREA INSTITUTE OF ENERGY RESEARCH, Daejeon (KR)

(72) Inventors: Il Hyun Baek, Daejeon (KR); Sung Chan Nam, Daejeon (KR)

(73) Assignee: Korea Institute of Energy Research, Daejeon (KR)

( * ) Notice: Subject to any disclaimer, the term of this patent is extended or adjusted under 35 U.S.C. 154(b) by 218 days.

(21) Appl. No.: 16/772,118

(22) PCT Filed: Mar. 27, 2020

(86) PCT No.: PCT/KR2020/004190
§ 371 (c)(1),
(2) Date: Jun. 11, 2020

(87) PCT Pub. No.: WO2020/262804
PCT Pub. Date: Dec. 30, 2020

(65) Prior Publication Data
US 2022/0161224 A1    May 26, 2022

(30) Foreign Application Priority Data
Jun. 27, 2019  (KR) .......................... 10-2019-0076963

(51) Int. Cl.
*B01D 53/14* (2006.01)
*B01J 20/08* (2006.01)
(Continued)

(52) U.S. Cl.
CPC .............. *B01J 20/08* (2013.01); *B01D 53/02* (2013.01); *B01D 53/04* (2013.01); *B01D 53/1425* (2013.01); *B01D 53/1462* (2013.01); *B01D 53/1468* (2013.01); *B01D 53/1475* (2013.01); *B01D 53/1493* (2013.01); *B01D 53/18* (2013.01); *B01D 53/52* (2013.01); *B01D 53/526* (2013.01); *B01D 53/62* (2013.01); *B01D 53/78* (2013.01); *B01J 8/02* (2013.01); *B01J 20/06* (2013.01); *B01J 20/20* (2013.01); *B01J 20/261* (2013.01); *B01J 20/28016* (2013.01); *B01J 20/28019* (2013.01); *C01B 3/34* (2013.01); *C10K 1/004* (2013.01); *C10K 1/143* (2013.01); *C10K 1/32* (2013.01); *C10L 3/103* (2013.01); *B01D 2251/602* (2013.01); *B01D 2252/20405* (2013.01); *B01D 2252/20421* (2013.01); *B01D 2252/20426* (2013.01); *B01D 2252/20431* (2013.01); *B01D 2252/20489* (2013.01);
(Continued)

(58) Field of Classification Search
None
See application file for complete search history.

(56) References Cited

U.S. PATENT DOCUMENTS 9,713,790 B2 * 7/2017 Jeong ..................... B01D 53/62
2016/0193563 A1 * 7/2016 Bumb ................ B01D 53/1425
252/192

FOREIGN PATENT DOCUMENTS

CA        3032652 A1 *  8/2018  ......... B01D 53/1425
DE  102009009753 A1 *  9/2010  ......... B01D 53/1425
KR  10-2014-0044807 A    4/2014

* cited by examiner

*Primary Examiner* — Daniel Berns
(74) *Attorney, Agent, or Firm* — Rabin & Berdo, P.C.

(57) ABSTRACT

Disclosed is an absorbent containing an amine for absorption of an acid gas in a biogas, and a biogas purification system using the same.

6 Claims, 23 Drawing Sheets

(51) Int. Cl.
*B01D 53/04* (2006.01)
*B01D 53/52* (2006.01)
*B01D 53/78* (2006.01)
*B01J 20/06* (2006.01)
*B01J 20/20* (2006.01)
*B01J 20/26* (2006.01)
*B01J 20/28* (2006.01)
*C01B 3/34* (2006.01)
*C10K 1/00* (2006.01)
*C10K 1/32* (2006.01)
*C10L 3/10* (2006.01)
*B01D 53/02* (2006.01)
*B01D 53/18* (2006.01)
*B01D 53/62* (2006.01)
*B01J 8/02* (2006.01)
*C10K 1/14* (2006.01)

(52) U.S. Cl.
CPC ............ *B01D 2252/504* (2013.01); *B01D 2253/102* (2013.01); *B01D 2253/1124* (2013.01); *B01D 2256/22* (2013.01); *B01D 2257/304* (2013.01); *B01D 2257/504* (2013.01); *B01D 2258/05* (2013.01); *B01J 2220/46* (2013.01); *C01B 2203/0205* (2013.01); *C01B 2203/1241* (2013.01); *C01B 2203/1258* (2013.01); *C10L 2290/542* (2013.01)

- SRM: Steam Reforming of Methane
- CDR: Carbon Dioxide Reforming Methane
- FT: Fisher-Tropsch Before calcination
(ZnO + AC + Binder)

After calcination at 850 ℃

FIG. 31

| | | GAS-IN | GAS-IN | MDEA-IN | RICH |
|---|---|---|---|---|---|
| Substream: MIXED | | | | | |
| Mole Flow kmol/hr | | | | | |
| N2 | | 0 | 0 | 0 | 0 |
| H2O | | 0 | 0.0843803 | 354.015 | 353.93 |
| H2S | | 0.00097247 | 1.01112e-06 | 0 | 0.000976679 |
| MDEA | | 0 | 4.47536e-06 | 38.9238 | 59.9229 |
| PZ | | 0 | 0 | 0 | 0 |
| CH4 | | 6.80729 | 1.59937 | 0 | 5.20792 |
| CO2 | | 2.91644 | 0.000244979 | 0 | 2.91619 |

ACID GAS ABSORBENT IN BIOGAS AND BIOGAS PURIFICATION SYSTEM USING THE SAME

TECHNICAL FIELD

The present invention relates to acid gas absorbent in biogas and biogas purification system using the same.

BACKGROUND ART

Fossil fuels are currently the world's primary energy source, yet they are finite resources. The burning of fossil fuels is responsible for emissions of greenhouse gases, such as carbon monoxide, carbon dioxide, sulfur, and nitrogen oxides. Those greenhouse gases contribute to global warming. Therefore, many studies have been made on clean energy resources as an alternative solution to the fossil fuels. Among the various sources that have been explored, biogas utilizing organic waste resources has attracted wide attention.

To convert biogas into high value-added products, such as synthetic oil, electric power and methane, gasification is achieved by reacting biomass with oxygen and/or steam under high-temperature and high-pressure conditions to obtain a syngas (synthetic gas $H_2/CO$). The syngas is burned in gas engines or used in the Fischer-Tropsch process for conversion. Yet the biogas using organic waste resources contains impurities ($H_2S$, $NH_3$, $H_2O$). In the presence of hydrogen sulfide ($H_2S$), nickel (Ni) catalysts used in the reforming process and iron (Fe) and cobalt (Co) catalysts in the Fischer-Tropsch (F-T) process are poisoned and deteriorated in performance. To prevent poisoning and deterioration of the catalysts by $H_2S$, the $H_2S$ concentration needs to be maintained at a level of 10 ppb or less. For this, exploring high-grade purification techniques for removal of $H_2S$ in biogas is essential.

General $H_2S$ removal methods can be categorized into adsorption using solid adsorbents, such as zeolite, iron oxide powder and impregnated activated carbons; Claus process; amine-based absorption; ammonia-based absorption; alkali-salt-based absorption; microorganism/enzyme-based process; and liquid catalyst-based oxidation-reduction. These conventional methods have disadvantages that they involve large-scaled equipment, deterioration of adsorption/absorption capacity, and long removal time, and even result in failure to reduce the $H_2S$ concentration in the biogas to a level of 10 ppb or below.

Korea Patent Laid-Open Publication No. 2014-0044807 discloses a method and system for separation and purification of methane from biogas that involves feeding biogas to a scrubber or an adsorption unit to remove the biogas of hydrogen sulfide ($H_2S$) and treating non-methane organic compounds in the liquid/gas phase. Yet the method is ineffective in performing high-grade removal of $H_2S$ in the biogas and requires additional large-capacity facilities. Therefore, there is a demand for biogas purification methods for removing $H_2S$ to the maximum degree with small-scale equipment.

DISCLOSURE OF INVENTION

Technical Problem

To solve the problems with the prior art, it is an object of the present invention to provide an absorbent containing amine for absorption of an acid gas in a biogas.

It is another object of the present invention to provide a biogas purification system using the absorbent.

The above objects of the invention are not intended as a definition of the limits of the invention. The above and other objects and features of the invention will become apparent for those skilled in the art from the following description of embodiments.

Technical Solution

In one aspect of the present invention to achieve the aforementioned objects, there is provided an absorbent for absorption of an acid gas in a biogas, which absorbent includes: a tertiary amine represented by the following chemical formula 1; a primary or secondary amine; and a solvent.

[Chemical Formula 1]

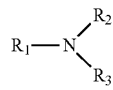

In the chemical formula 1, R1 is linear or branched C1-C5 alkyl or linear or branched C2-C5 alkenyl; and R2 and R3 are independently linear or branched C1-C10 alkyl having a terminal thereof unsubstituted or substituted with a hydroxyl group, or linear or branched C2-C10 alkenyl having a terminal thereof unsubstituted or substituted with a hydroxyl group, where at least either one of the R2 and R3 is linear or branched C1-C10 alkyl having a terminal thereof substituted with a hydroxyl group, or linear or branched C2-C10 alkenyl having a terminal thereof substituted with a hydroxyl group.

In the chemical formula 1, R1 may be linear C1-C3 alkyl or linear C2-C3 alkenyl; and R2 and R3 may be independently linear or branched C1-C5 alkyl having a terminal thereof unsubstituted or substituted with a hydroxyl group, or linear or branched C2-C5 alkenyl having a terminal thereof unsubstituted or substituted with a hydroxyl group.

In the chemical formula 1, R1 may be linear C1-C3 alkyl; and R2 and R3 may be independently linear or branched C1-C5 alkyl having a terminal thereof unsubstituted or substituted with a hydroxyl group.

The tertiary amine represented by the chemical formula 1 may be methyl diethanolamine (MDEA).

The primary or secondary amine may include any one amine selected from the group consisting of AMP (2-amino-2-methyl-1-propanol), TEPA (tetraethylenepentamine), DETA (diethylenetriamine), APA(bis(3-aminopropyl) amine), DAB(1,4-diaminobutane), DBA (dibutylamine), AB(2-amino-1-butanol), AP(5-amino-1-pentanol), PED(N-propylethylenediamine), DEP(1-dimethylamino-2-propanol), PA(1-propanamine), DPA(N-propyl-propanamine), BA(1-butanamine), IBA(2-methyl-1-propanamine), SBA(2-butanamine), PZ(piperazine), 1,2-dimethylpropylamine, 3-methyl-2-butanamine, hexylamine, allylamine, diallylamine, 3-methoxy propylamine, 3-ethoxyl propylamine, 3-propoxypropylamine, 3-isopropoxy propylamine, 3-butoxyl propylamine, 3-decyloxypropylamine, 3-lauryloxy propylamine, dimethylamino ethylamine, ethylaminoethylamine, 1,2-diaminopropane, 1,3-diamino propane, N,N-diethyl-1,3-propanediamine, dibutylamino propylamine, bis-(3-aminopropyl) ether, 1,2-diaminobutane, 1,4-diaminobutane, and combinations thereof.

The content of the primary or secondary amine may be 5 to 50 parts by weight with respect to 100 parts by weight of the tertiary amine.

The content of the tertiary amine may be 1 to 85 parts by weight with respect to 100 parts by weight of the absorbent.

The biogas may include 20 to 50 vol % of methane ($CH_4$), 5 to 30 vol % of carbon dioxide ($CO_2$), and 5 to 30,000 ppm of hydrogen sulfide ($H_2S$).

The acid gas may include any one gas selected from the group consisting of carbon dioxide ($CO_2$), hydrogen sulfide ($H_2S$), sulfur dioxide ($SO_2$), sulfur trioxide ($SO_3$), carbonyl sulfide (COS), carbon disulfide ($CS_2$), mercaptan (RSH), and combinations thereof.

In another aspect of the present invention, there is provided a biogas purification system using the absorbent, which system includes: a biogas generator for producing a biogas including methane ($CH_4$) and an acid gas; and a first biogas purifier for using the above-specified absorbent to separate the methane and the acid gas from the produced biogas.

The biogas purification system may further include: a second biogas purifier for using an adsorbent to remove hydrogen sulfide ($H_2S$) from the acid gas separated in the first biogas purifier and discharging carbon dioxide ($CO_2$); and a reformer for producing a syngas using the methane discharged from the first biogas purifier and the carbon dioxide discharged from the second biogas purifier. The adsorbent may include a metal oxide, an additive, and a binder.

EFFECTS OF INVENTION

In accordance with an embodiment of the present invention, the absorbent for absorption of an acid gas in a biogas includes both a primary or secondary amine and a tertiary amine, by which it can absorb the acid gas such as carbon dioxide and/or hydrogen sulfide in the biogas with high absorption efficiency and ensure high regeneration efficiency as well.

Further, the biogas purification system using the absorbent involves an excellent process for converting biogas into clean energy fuel and relatively low operating costs, so it is very beneficial in the aspect of economy.

The above effects of the invention are not intended as a definition of the limits of the invention, but they may be understood to include all the effects derivable from the configuration of the present invention specified in the following detailed description and claims of the present invention.

BRIEF DESCRIPTION OF FIGURES

(FIG. 21a) breakthrough curves; and (FIG. 21b), (FIG. 21c) the amount of adsorbed $H_2S$.

(FIG. 22a) breakthrough curves; and (FIG. 22b), (FIG. 22c) the amount of adsorbed H₂S.

(FIG. 23a) breakthrough curves; and (FIG. 23b), (FIG. 23c) the amount of adsorbed H₂S.

(FIG. 24a) breakthrough curves; and (FIG. 24b) the amount of adsorbed H₂S.

(FIG. 25a) breakthrough curves; and (FIG. 25b) the amount of adsorbed H₂S.

(FIG. 26a) breakthrough curves; and (FIG. 26b), (FIG. 26c) the amount of adsorbed H₂S.

FIG. 31 presents the results of an ASPEN process simulation of H₂S absorption using absorbents in accordance with an embodiment of the present invention.

BEST MODES FOR CARRYING OUT THE INVENTION

Figure 1:
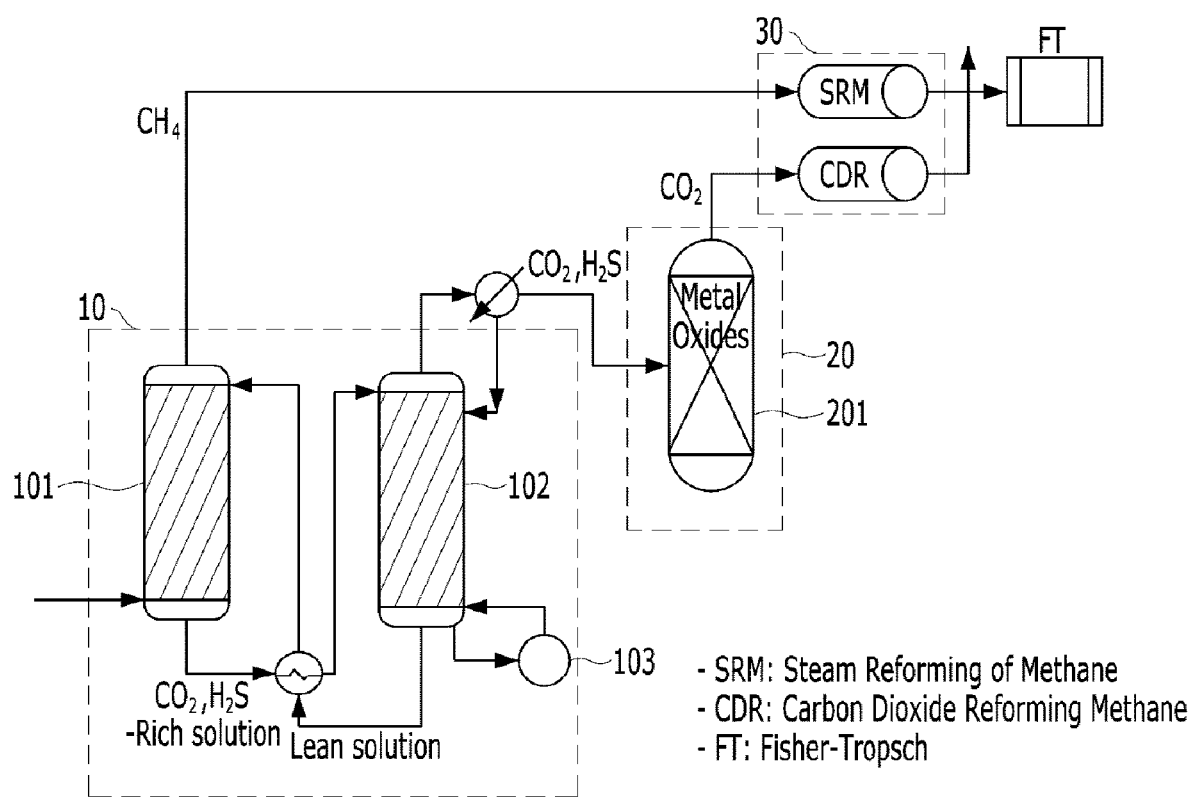
FIG. 1 is a schematic diagram of a biogas purification system for producing clean energy fuels in accordance with an embodiment of the present invention.

Hereinafter, the present invention will be described in further detail with reference to examples. It will be obvious to those skilled in the art that these examples are illustrative purposes only and are not intended to limit the scope of the present invention.

The terminology used herein is for the purpose of describing an embodiment only and is not intended to be limiting of an exemplary embodiment. As used herein, the singular forms are intended to include the plural forms as well, unless the context clearly indicates otherwise. It will be further understood that the terms "comprises" and/or "comprising" and "includes" and/or "including" when used in this specification, specify the presence of stated components but do not preclude the presence or addition of one or more other components.

In a first aspect of the present invention, there is provided an absorbent for absorption of an acid gas in a biogas, which absorbent includes: a tertiary amine represented by the following chemical formula 1; a primary or secondary amine; and a solvent.

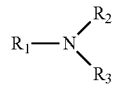

[Chemical Formula 1]

In the chemical formula 1, R1 is linear or branched C1-C5 alkyl or linear or branched C2-C5 alkenyl; and R2 and R3 are independently linear or branched C1-C10 alkyl having a terminal thereof unsubstituted or substituted with a hydroxyl group, or linear or branched C2-C10 alkenyl having a terminal thereof unsubstituted or substituted with a hydroxyl group, where at least either one of the R2 and R3 is linear or branched C1-C10 alkyl having a terminal thereof substituted with a hydroxyl group, or linear or branched C2-C10 alkenyl having a terminal thereof substituted with a hydroxyl group.

Hereinafter, a detailed description will be given as to the absorbent for absorption of an acid gas in a biogas according to the first aspect of the present invention.

In an embodiment of the present invention, the absorbent for absorption of an acid gas in a biogas may include a tertiary amine represented by the chemical formula 1. The tertiary amine may form a direct chemical bonding to the hydrogen sulfide or carbon dioxide in the acid gas to absorb the hydrogen sulfide or carbon dioxide. Preferably, in the chemical formula 1, R1 may be linear C1-C3 alkyl or linear C2-C3 alkenyl; and R2 and R3 may be independently linear or branched C1-C5 alkyl having a terminal thereof unsubstituted or substituted with a hydroxyl group, or linear or branched C2-C5 alkenyl having a terminal thereof unsubstituted or substituted with a hydroxyl group. More preferably, in the chemical formula 1, R1 may be linear C1-C3 alkyl; and R2 and R3 may be independently linear or branched C1-C5 alkyl having a terminal thereof unsubstituted or substituted with a hydroxyl group. According to an embodiment of the present invention, the tertiary amine represented by the chemical formula 1 may be methyl diethanolamine (MDEA).

In an embodiment of the present invention, the absorbent for absorption of an acid gas in a biogas may further include a primary amine or a secondary amine in addition to the tertiary amine of the chemical formula 1. The primary or secondary amine may function to increase the acid gas absorption rate of the absorbent. Specifically, the primary or secondary amine may include any one amine selected from the group consisting of AMP(2-amino-2-methyl-1-propanol), TEPA(tetraethylenepentamine), DETA(diethylenetriamine), APA(bis(3-aminopropyl)amine), DAB(1,4-diaminobutane), DBA(dibutylamine), AB(2-amino-1-butanol), AP(5-amino-1-pentanol), PED(N-propylethylenediamine), DEP(1-dimethylamino-2-propanol), PA(1-propanamine), DPA(N-propyl-propanamine), BA(1-butanamine), IBA(2-methyl-1-propanamine), SBA(2-butanamine), PZ(piperazine), 1,2-dimethylpropylamine, 3-methyl-2-butanamine, hexylamine, allylamine, diallylamine, 3-methoxy propylamine, 3-ethoxyl propylamine, 3-propoxypropylamine, 3-isopropoxy propylamine, 3-butoxyl propylamine, 3-decyloxypropylamine, 3-lauryloxy propylamine, dimethylamino ethylamine, ethylaminoethylamine, 1,2-diaminopropane, 1,3-diamino propane, N,N-diethyl-1,3-propanediamine, dibutylamino propylamine, bis-(3-aminopropyl) ether, 1,2-diaminobutane, 1,4-diaminobutane, and combinations thereof.

In an embodiment of the present invention, the content of the primary or secondary amine may be 5 to 50 parts by weight with respect to 100 parts by weight of the tertiary amine. Preferably, it may be 5 to 30 parts by weight, and more preferably 8 to 15 parts by weight with respect to 100 parts by weight of the tertiary amine. In an embodiment of the present invention, the mixing ratio (w/w) of the tertiary amine to the primary or secondary amine may be 1:9. If the content of the primary or secondary amine is less than 5 parts by weight with respect to 100 parts by weight of the tertiary amine, then the absorption rate for the acid gas in the biogas deteriorates due to the relatively low content of the primary or secondary amine used as an additive. If the content of the primary or secondary amine is greater than 50 parts by weight with respect to 100 parts by weight of the tertiary amine, then the absorption rate for the acid gas in the biogas declines due to the relatively low content of the tertiary amine used as a chief chemical constituent of the absorbent. That is, by mixing the primary or secondary amine with the tertiary amine at a proper weight ratio in the above-defined range, the absorbent of the present invention can show high levels of absorption rate and absorption efficiency for the acid gas in the biogas.

In an embodiment of the present invention, the content of the tertiary amine may be 1 to 85 parts by weight with respect to 100 parts by weight of the absorbent. Preferably, it may be 3 to 65 parts by weight, and more preferably 4 to 55 parts by weight with respect to 100 parts by weight of the absorbent. In an embodiment of the present invention, the content of the tertiary amine may be 40 wt % with respect to the total weight of the absorbent. If the content of the tertiary amine is less than 1 part by weight with respect to 100 parts by weight of the absorbent, then the absorption efficiency for the acid gas in the biogas deteriorates due to the relatively low content of the tertiary amine. If the content of the tertiary amine is greater than 85 parts by weight with respect to 100 parts by weight of the absorbent, then the viscosity of the absorbent is so high as to reduce the transfer of substances between the acid gas and the absorbent and thus to deteriorate the absorption efficiency. It also reduces heat transfer in a heat exchanger and inhibits an efficient use of heat, thereby increasing energy consumption.

In an embodiment of the present invention, the solvent is not specifically limited; but preferably, it may be water. The content of the solvent may be 10 to 99 parts by weight with respect to 100 parts by weight of the absorbent. In an embodiment of the present invention, the content of the solvent may be about 95 parts by weight with respect to 100 parts by weight of the absorbent.

In an embodiment of the present invention, the biogas may include methane ($CH_4$) and an acid gas. The acid gas may include any one gas selected from the group consisting of carbon dioxide ($CO_2$), hydrogen sulfide ($H_2S$), sulfur dioxide ($SO_2$), sulfur trioxide ($SO_3$), carbonyl sulfide (COS), carbon disulfide ($CS_2$), mercaptan (RSH), and combinations thereof. More specifically, the biogas may include 20 to 50 vol % of methane ($CH_4$), 5 to 30 vol % of carbon dioxide ($CO_2$), 5 to 30,000 ppm of hydrogen sulfide ($H_2S$), and other gas.

In an embodiment of the present invention, the absorbent may have a cyclic capacity for carbon dioxide in the range from 0.05 $mol_{CO2}/mol_{amine}$ to 0.07 $mol_{CO2}/mol_{amine}$, and a cyclic capacity for hydrogen sulfide in the range from $0.2 \times 10^{-4}$ $mol_{H2S}/mol_{amine}$ to $1.5 \times 10^{-4}$ $mol_{H2S}/mol_{amine}$. The term "cyclic capacity" refers to the difference between the values of rich loading and lean loading. The rich loading means absorption equilibrium at the completion of the acid gas absorption, and the lean loading means regeneration equilibrium at the completion of the acid gas absorption. In other words, the higher value of the rich loading and the lower value of the lean loading indicate the higher absorption efficiency of the absorbent for the acid gas. Therefore, the higher value of the cyclic capacity, that is, the greater difference between the values of rich loading and lean loading renders the absorbent having the higher absorption efficiency. More specifically, the absorbent may have a $CO_2$ rich loading value of 0.05 to 0.08 $mol_{CO2}/mol_{amine}$ and a $CO_2$ lean loading value of 0.001 to 0.02 $mol_{CO2}/mol_{amine}$. Further, the absorbent may have a $H_2S$ rich loading value from $0.5 \times 10^{-4}$ $mol_{H2S}/mol_{amine}$ to $2.0 \times 10^{-4}$ $mol_{CO2}/mol_{amine}$, and a $H_2S$ lean loading value from $0.25 \times 10^{-4}$ $mol_{H2S}/mol_{amine}$ to $0.75 \times 10^{-4}$ $mol_{H2S}/mol_{amine}$ On the other hand, the absorbent may have high absorption and regeneration rates for the acid gas. More specifically, the absorbent may have an absorption rate for carbon dioxide in the range from $0.25 \times 10^{-3}$ $mol_{CO2}/min$ to $1.25 \times 10^{-3}$ $mol_{CO2}/min$, preferably from $0.5 \times 10^{-3}$ $mol_{CO2}/min$ to $1.25 \times 10^{-3}$ $mol_{CO2}/min$. Further, the absorbent may have a regeneration rate for carbon dioxide in the range from $0.1 \times 10^{-3}$ $mol_{CO2}/min$ to $1.0 \times 10^{-3}$ $mol_{CO2}/min$, preferably from $0.25 \times 10^{-3}$ $mol_{CO2}/min$ to $1.0 \times 10^{-3}$ $mol_{CO2}/min$. Further, the absorbent may have an absorption rate for hydrogen sulfide in the range from $0.5 \times 10^{-6}$ $mol_{H2S}/min$ to $1.5 \times 10^{-6}$ $mol_{H2S}/min$, preferably from $0.75 \times 10^{-6}$ $mol_{H2S}/min$ to $1.5 \times 10^{-6}$ $mol_{H2S}/min$. Further, the absorbent may have a regeneration rate for hydrogen sulfide in the range from $0.25 \times 10^{-6}$ $mol_{H2S}/min$ to $2.0 \times 10^{-6}$ $mol_{H2S}/min$, preferably from $1.0 \times 10^{-6}$ $mol_{H2S}/min$ to $2.0 \times 10^{-6}$ $mol_{H2S}/min$.

In a second aspect of the present invention, there is provided a biogas purification system using the absorbent of the first aspect of the present invention, which system includes: a biogas generator for producing a biogas including methane ($CH_4$) and an acid gas; and a first biogas purifier for using the absorbent of the first aspect of the present invention to separate the methane and the acid gas from the produced biogas.

For the constituent parts identical to those described in association with the first aspect of the present invention, redundant description is omitted in the second aspect of the present invention, but the same context of the first aspect of the present invention will be applied to like parts in the second aspect of the present invention.

Hereinafter, a detailed description will be given as to the biogas purification system according to the second aspect of the present invention with reference to FIG. 1, which is a schematic diagram of the biogas purification system.

In an embodiment of the present invention, the biogas purification system may purify a biogas produced by the biogas generator. The biogas generator may produce a biogas in an anaerobic digestion bath for producing methane from organic waste resources. The biogas produced in the anaerobic digestion bath includes impurities like acid gas, such as carbon dioxide and hydrogen sulfide, in addition to methane. The biogas purification system of the present invention may be a system for high-grade purification of the acid gas in the biogas, particularly hydrogen sulfide. The biogas normally produced in the anaerobic digestion bath consists of 25~50% carbon dioxide, 50~75% methane, 0~0.5% hydrogen sulfide, 0.05% ammonia, and 1~5% water vapor. Yet, the present invention improves the anaerobic digestion bath in order to achieve high-grade purification of hydrogen sulfide, so the biogas generator may produce a biogas containing 10 to 70 wt % of methane, 1 to 30 wt % of carbon dioxide, and 5 to 30,000 ppm of hydrogen sulfide, preferably 100 ppm of hydrogen sulfide. In an embodiment of the present invention, the substrate used in the anaerobic digestion bath may be subjected to pre-treatment of hydrogen sulfide using the symbiotic relationship between sulfur-reducing bacteria and acid fermenters according to the $H_2S$ removal technique. Due to sulfur-reducing bacteria having fast growth rate and high affinity to the substrate, sulfates are reduced to hydrogen sulfide in the pre-treatment reaction bath dominated by the sulfur-reducing bacteria. For obtaining a stably desulfurized biogas, removal of hydrogen sulfide is necessary prior to producing the biogas in the anaerobic digestion bath. The biogas produced in the anaerobic digestion bath may be fed to a first biogas purifier 10.

In an embodiment of the present invention, the first biogas purifier 10 is for separating methane and other acid gas in the biogas. That is, the first biogas purifier 10 may involve a process of using a liquid absorbent to remove acid gas, such as hydrogen sulfide and carbon dioxide, other than methane, and include an absorption tower 101 and a regeneration tower 102. In the first biogas purifier 10, the absorption tower 101 chemically absorbs hydrogen sulfide and carbon dioxide contained in the biogas and discharges methane, and the regeneration tower 102 receives an absorbent solution impregnated with the hydrogen sulfide and the carbon dioxide and regenerates the absorbent. The isolated methane is discharged to the top of the absorption tower and fed to a reformer 30. The absorption tower 101 is an apparatus for absorbing carbon dioxide and hydrogen sulfide with a liquid absorbent. For example, while being sprayed from the top of the absorption tower, the liquid absorbent can absorb the acid gas such as carbon dioxide and hydrogen sulfide from the biogas fed to the bottom of the absorption tower. The absorbent is specifically described in association with the first aspect of the present invention, and redundant description should be omitted in the second aspect of the present invention.

In an embodiment of the present invention, the absorbent impregnated with hydrogen sulfide and carbon dioxide in the absorption tower 101 is fed to the regeneration tower 102 to release the hydrogen sulfide and the carbon dioxide. Removed of the hydrogen sulfide and the carbon dioxide, the absorbent is captured, regenerated, and fed back to the absorption tower 101 for a recycle. The bottom of the regeneration tower 102 is connected to a re-boiler to receive hot steam, which is for use in the regeneration of the absorbent impregnated with carbon dioxide and hydrogen sulfide while the absorbent is entering the regeneration tower 102. The regenerated absorbent is fed back to the absorption tower 101. The treated gas including the hydrogen sulfide and carbon dioxide released from the absorbent in the regeneration tower 102 is fed to a second biogas purifier 20.

In an embodiment of the present invention, the biogas purification system may further include: a second biogas purifier 20 for using an adsorbent to remove hydrogen sulfide ($H_2S$) from the acid gas separated in the first biogas purifier and discharging carbon dioxide ($CO_2$); and a reformer 30 for producing a syngas using the methane discharged from the first biogas purifier 10 and the carbon dioxide discharged from the second biogas purifier 20.

In an embodiment of the present invention, the second biogas purifier 20 may include an adsorption tower 201. The treated gas is supplied for an adsorbent equipped in a fixed-bed reactor of the adsorption tower 201 and gets removed of hydrogen sulfide and carbon dioxide, which carbon dioxide is discharged. The adsorbent may include a metal oxide, an additive, or a binder and have advantages of displaying selectivity to certain substances, specific surface area, durability and formability that can be maintained at certain high levels even after long-term uses.

In an embodiment of the present invention, the metal oxide may include any one substance selected from the group consisting of $ZnO$, $Fe_2O_3$, $CoO$, $CuO$, $NiO_2$, $Ni_2O_3$, $NiO$, $ZrO_2$, $V_2O_5$, $MoO_3$, $WO_3$, $TiO_2$, $Cr_2O_3$, $Ag_2O$, $MnO_3$, $Mn_2O_3$, $Al_2O_3$, $Na_2O$, $Li_2O$, $Rh_2O_3$, $RhO_2$, $K_2O$, $PdO$, $LiCoO_2$, and combinations thereof. The additive may include any one substance selected from the group consisting of active carbon, boehmite, zeolite, clay, alumina ($Al_2O_3$), silica ($SiO_2$), and combinations thereof. The binder may include any one substance selected from the group consisting of polyvinyl alcohol (PVA), bentonite, methyl cellulose, carbohydrate, carboxylic methyl cellulose, and combinations thereof.

In an embodiment of the present invention, the proper content of the additive may vary depending on the type of the metal oxide. When the metal oxide is $ZnO$, for example, the proper content of the additive may be 7.5 to 15 parts by weight with respect to 100 parts by weight of the adsorbent. When the metal oxide is $Fe_2O_3$, the proper content of the additive may be 10 to 20 parts by weight with respect to 100 parts by weight of the adsorbent. When the metal oxide is $CuO$, the proper content of the additive may be 20 to 90 parts by weight with respect to 100 parts by weight of the adsorbent. In the case of the metal oxide being $CuO$, more specifically, the additive may be active carbon and/or boehmite. When the boehmite is used alone, the content of the boehmite may be 80 to 90 parts by weight with respect to 100 parts by weight of the adsorbent. When the additive is a mixture of active carbon and boehmite, the content of the active carbon may be 20 to 33 parts by weight with respect to 100 parts by weight of the adsorbent, and the content of the boehmite may be 34 to 60 parts by weight with respect to 100 parts by weight of the adsorbent. In other words, the adsorbent can display high hydrogen sulfide adsorption capacity by selecting a proper mixing ratio (w/w) of the metal oxide to the additive depending on the types of the metal oxide and the additive.

The adsorbent may be a mixture of two metal oxides only. For example, the adsorbent may be a mixture of $CoO$ and $ZnO$, in which case the mixing ratio (w/w) of $CoO$ to $ZnO$ may be 1:0.1 to 3; or $CoO$ may be used alone.

Most preferably, the adsorbent may be a mixture of metal oxides that includes $CuO$, $ZnO$, and $Al_2O_3$. In this case, the content of $CuO$ may be 30 to 80 parts by weight, preferably 45 to 80 parts by weight, and more preferably 60 to 80 parts by weight, with respect to 100 parts by weight of the mixture. That is, the $H_2S$ adsorption capacity of the adsorbent may increase with an increase in the content of $CuO$ in the composition of the metal oxide. When the metal oxide is a mixture of $CuO$, $ZnO$ and $Al_2O_3$, the additive may be boehmite and the binder may be polyvinyl alcohol (PVA). In this case, the content of the metal oxide mixture may be 5 to 95 parts by weight with respect to 100 parts by weight of the adsorbent, and the content of the additive may be 5 to 95 parts by weight with respect to 100 parts by weight of the adsorbent. Namely, the $H_2S$ adsorption capacity of the adsorbent may be high when the content of the metal oxide mixture is in the above-defined range. The adsorbent including the mixture of $CuO$, $ZnO$ and $Al_2O_3$, for example, may have a $H_2S$ adsorption capacity ranging from 35 mg $H_2S$/g to 60 mg $H_2S$/g.

In an embodiment of the present invention, in order to implement the composition and shape of the adsorbents favorable to adsorption, the adsorbent may be formed from the metal oxide, the additive and the binder through the steps of mixing, kneading, extrusion, drying, and plastic forming, and it may be provided in the form of a pellet. That is, the present invention infers the conditions for the addition of a binder and the plastic forming process in view of the formation of an adsorbent optimized for H$_2$S adsorption. The adsorbent molded in the form of a pellet, specifically in the shape of a continuous cylinder, has a high H$_2$S adsorption capacity, which is demonstrated in the examples of the present invention as stated below. The adsorbent thus prepared may have a H$_2$S adsorption capacity from 25 mg H$_2$S/g to 60 mg H$_2$S/g. The CO$_2$-rich gas that is removed of hydrogen sulfide in the second biogas purifier 20 may be fed to a reformer 30.

In an embodiment of the present invention, the reformer 30 may produce a syngas using the methane discharged from the first biogas purifier 10 and the carbon dioxide discharged from the second biogas purifier 20. For example, the syngas may be prepared by steam reforming of methane (SRM) and carbon dioxide reforming of methane (CDR). The SRM method involves a reaction between methane and steam to form carbon monoxide and hydrogen (CH$_4$+H$_2$O→CO+ 3H$_2$, ΔH°=206 kJ/mol) under the pressure of 1 to 40 atm, with a temperature of 700 to 850° C. and a space velocity of 3,000 to 6,000 hr$^{-1}$. The carbon dioxide reforming of methane (CDR) method reacts methane and carbon dioxide to form carbon monoxide and hydrogen (CH$_4$+CO$_2$→2CO+ 2H$_2$, ΔH°=247 kJ/mol) under the pressure of 1 to 10 atm with a temperature of 700 to 850° C. The syngas thus obtained may be used as it is or converted into value-added chemicals through a Fisher-Tropsch (F-T) reactor. The Fisher-Tropsch (F-T) process involves a conversion of the syngas into synthetic fuel and consists of the four chemical reactions given as follows, which reactions take place in the presence of iron or cobalt catalysts under the pressure of 10 to 30 atm with a temperature of 200 to 350° C. In the present invention, methane and carbon dioxide are produced from the biogas removed of hydrogen sulfide through high-grade purification, so the performance deterioration of the catalyst used in the T-F reactions can be avoided.

(a) Chain growth in FT synthesis

$$CO+2H_2 \rightarrow -CH^{2-}+H_2O \; \Delta H(227° \text{C.})=-165 \text{ kJ/mol}$$

(b) Methanation

$$CO+3H_2 \rightarrow CH_4+H_2O \; \Delta H(227° \text{C.})=-215 \text{ kJ/mol}$$

(c) Water gas shift reaction

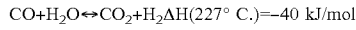
$$CO+H_2O \leftrightarrow CO_2+H_2 \Delta H(227° \text{C.})=-40 \text{ kJ/mol}$$

(d) Boudouard reaction

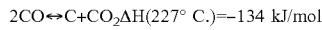
$$2CO \leftrightarrow C+CO_2 \Delta H(227° \text{C.})=-134 \text{ kJ/mol}$$

In an embodiment of the present invention, the process for converting biogas into syngas through the first and second biogas purifiers 10 and 20 in the biogas purification system may separate methane taking up about 70% of the biogas in the first biogas purifier 10 and remove hydrogen sulfide only from a small amount of the treated gas through the adsorption tower 201 of the second biogas purifier 20, resulting in achieving a high level of H$_2$S removal and extending the size and life cycle of the process.

In further another aspect of the present invention, there is provided a biogas purification method for production of a clean energy fuel, which method may include: producing a biogas in an anaerobic digestion bath; feeding the biogas to a first biogas purifier 10 to separate an acid gas including hydrogen sulfide and carbon dioxide from the biogas with a liquid absorbent and discharge methane and the acid gas; feeding the acid gas discharged from the first biogas purifier 10 to a second biogas purifier 20 to remove hydrogen sulfide from the acid gas with an adsorbent; and converting the methane discharged from the first biogas purifier 10 and the carbon dioxide from the second biogas purifier 20 into a syngas in a reformer 30. The first biogas purifier 10 may include an absorption tower 101 for absorbing the acid gas with an absorbent, and a regeneration tower 102 for regenerating the absorbent impregnated with the acid gas. The absorbent may include a tertiary amine and a primary or secondary amine. The adsorbent may include a metal oxide, an additive, and a binder. The composition of the biogas, the absorbent and the adsorbent may have the same specifications as stated above. Yet, the method may further include feeding the syngas produced in the reformer 30 to a Fisher-Tropsch (F-T) reactor to convert the syngas into a fuel and chemical compounds. The biogas purification method of the present invention removes the biogas of hydrogen sulfide to a high degree to maintain the content of hydrogen sulfide in the biogas not more than 10 ppb, which consequently prevents performance deterioration of the catalysts used under necessary in the F-T reactions through reforming, so it may be effective in production of value-added compounds.

Hereinafter, a detailed description will be given as to the examples of the present invention in order for those skilled in the art to embody the present invention with ease. Many modifications and variations are possible, and the embodiments of the present invention disclosed herein are not construed to limit the scope of the invention.

Example 1: Separation of Acid Gas in Biogas with Absorbent

1. Materials

The selected absorbent used an additive based on MDEA (99%, Sigma-Aldrich). All materials were used without further purification. Examples of the additive as used herein include: PZ (Sigma-Aldrich), AMP (99%, Sigma-Aldrich), TEPA (Sigma-Aldrich), DETA (Sigma-Aldrich), 1-dimethylamino propanol (99%, Sigma-Aldrich), bis(3-aminopropyl)amine (98%, Sigma-Aldrich), 2-amino-1-butanol (97%, Sigma-Aldrich), 5-amino-1-pentanol (>95%, TCI), N-12 amines of propylethylenediamine (99%, Sigma-Aldrich), 1,4-diaminobutane (99%, Sigma-Aldrich), and dibutylamine (≥99.5%, Sigma-Aldrich). The gas used in the experiment was CO$_2$ (99.9%), N$_2$ (99.9%) and H$_2$S (100 ppm+N$_2$ balance); all gas was purchased from Korea Nano Gas. The silicon oil used for the control of absorption and regeneration temperatures was XIAMETER PMX-200 Dow Corning.

2. Experimental Analysis

Figure 2:
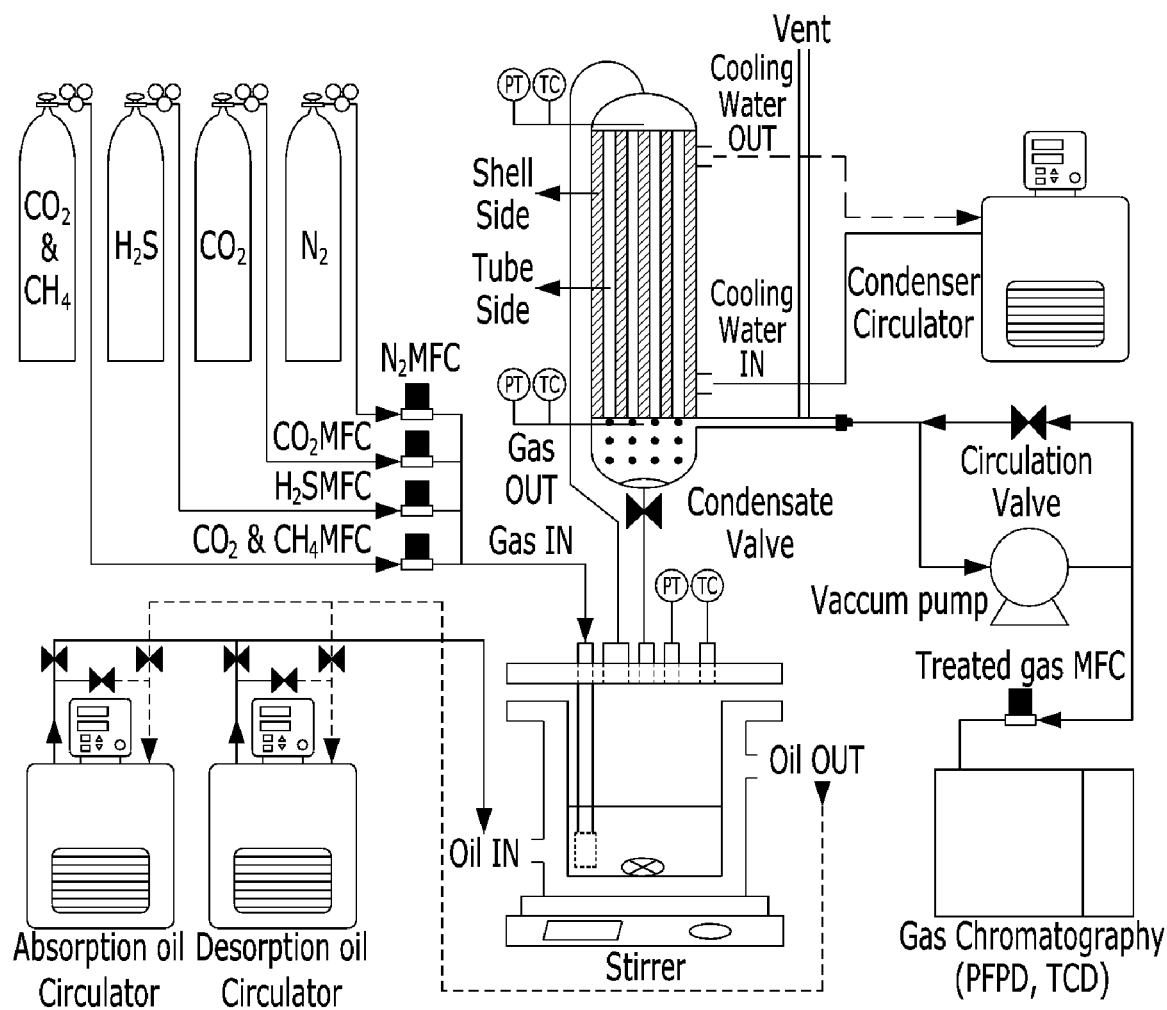
FIG. 2 is a schematic diagram of an experimental setup for simultaneous absorption and regeneration of $CO_2$ and $H_2S$ in accordance with an embodiment of the present invention.

The absorption and regeneration device used in the experiment is shown in FIG. 2. The reactor consisted of a 250 mL jacketed reactor for absorption and regeneration temperatures. The absorbent (100 g) in the reactor was put into the experiment. The oil entering the reactor jacket to maintain the temperature in absorption and regeneration was maintained by using two RW-2025G products of JeioTech. In the initial condenser experiment of the basic experiment, it was found that a large amount of water volatilized upon regeneration. In order to solve this problem, a stainless steel condenser of a shell and tube type was manufactured instead of glass condenser. The fabricated shell and tube condenser showed an evaporation rate of 0.1-0.15 g/h in 20 consecutive experiments (for 120 h) of absorption (at 35° C.) and regeneration (at 80-150° C.). After the reaction in the reactor, the gas entered the top of the shell and tube condenser. Since the regeneration was performed at 80-150° C., the condenser temperature was maintained at 2° C. in a heat duty condenser with condensation capacity higher than the used condenser's. Condensation performance was confirmed by measuring the temperature at the top and bottom of the condenser, and the temperature inside the reactor during regeneration. In order to deliver gas at a constant flow rate after treatment in the gas chromatograph, the gas was injected using LABOPORT N86KT from KNF (Germany).

3. Gas Analysis After the absorption and regeneration experiment, the gas was consistently sent to analysis equipment at a flow rate of ±100 mL/min using a sampling pump. After the rest of the treatment, the gas was vented. In order to maintain the overall composition of the gas and the atmospheric pressure constant in the reactor, the inlet and outlet openings of the vacuum pump was connected to control the valve, and a defined amount of the gas was sent to the analysis equipment. For gas analysis, an Agilent 7890A GC (Gas Chromatography) pulsed flame photometric detector and a thermal conductivity detector were used. For $CO_2$, $N_2$ and $CH_4$ analysis, Supelco Analytical Porapak N column was used. For $H_2S$ analysis, J&W GS-GasPro column 30 m×0.32 mm×7 in. was used. Analytik Jena total organic carbon was used for the $CO_2$ liquid phase analysis.

3-1. $CO_2$ and $H_2S$ Absorption

The experimental conditions in this experimental example were conducted to compare the absorption and regeneration capacities of MDEA-based additives. When the amine absorbent absorbed the acid gas at 25, 35, and 45° C. intervals, the absorption loading value at 25° C. was highest. The biogas production temperature is normally in the range from 35° C. to 42° C., so it was set to 35° C. Setting the concentration of the absorbent is of great importance. The concentration of $H_2S$ used in the experiment was in a ppm range, which was a small amount in relation to the $CO_2$ concentration. At a high concentration of the absorbent, the absorption capacity of $CO_2$ was comparable, but the trend of $H_2S$ was hard to confirm. With the $H_2S$ gas having a very high solubility to water, the absorption capacity for $H_2S$ gas alone was very high. Therefore, a low concentration (5 wt. %) of amine was used to confirm the pronounced trend of simultaneous absorption and regeneration of $CO_2$ and $H_2S$ under the same conditions. The total concentration of the amine absorbent composition was fixed at 5 wt. %, and the concentration for each constituent component was set as MDEA 4.5 wt. %+additive 0.5 wt. %. Under the defined experimental conditions of absorption, the reactor pressure was maintained at atmospheric pressure; the gas concentration was given as $CO_2$ (15 vol. %)+$N_2$ balance; and the gas flow rate was 200 mL/min. When using a mixed gas, the gas concentration was given as $CO_2$ (30 vol. %)+$N_2$ balance; $CO_2$ (30 vol. %)+$CH_4$ (70 vol. %) at 100 mL/min; $H_2S$ (100 ppm) $N_2$ balance at 100 mL/min; or $CO_2$ (15 vol. %)+$H_2S$ (50 ppm) at 200 mL/min. The gas was injected using a stainless steel gas muffler for miscibility of the gas flowing into the reactor. The amine solution was maintained at 500 rpm to fix the temperature in the reactor. The treated gas after absorption was analyzed by GC.

If V is calculated by substituting 1 atm, T ° C.=(273.15+T) K, and 1 mol from the ideal gas state equation PV=nRT, $$V=nRT/P=1 \text{ (mol)} \times 0.08206 \text{ (amt·L/mol·}K) \times (273.15+T)K/1 \text{ atm}=22.4 \text{ L(at 0° C.)}$$ [Equation 1]

$CO_2$ outlet gas×(1 mol/22.4 L)=$CO_2$ mol 3-2. $CO_2$ and $H_2S$ Desorption

In general, the biogas production temperature is from 35 to 42° C., so it was set at 35° C. based on the biogas production temperature. The regeneration temperature was set to 80° C. using an absorbent in the absorption equilibrium state, where absorption was completed. In the regeneration experiment, $N_2$ (170 mL/min) was injected to correct the concentration of $CO_2$ (15 vol. %). The regeneration of the MDEA+additive absorbent at 80° C. was compared. The complete regeneration of the MDEA 5 wt % amine absorbent with $CO_2$ was conducted at 105° C., and four temperature-dependent experiments were performed at 80, 90, 95, and 105° C.

4. Cyclic Capacity Measurement

The selected one of the MDEA-based additives was an absorbent having excellent absorption and regeneration capability in simultaneous absorption of $CO_2$ and $H_2S$. At the completion of the absorption, the absorption equilibrium is called "rich loading" and the regeneration equilibrium is called "lean loading". The difference between the rich loading and lean loading values is referred to as "cyclic capacity" (Refer to Equation 2). The cyclic capacity was used to confirm the absorption and regeneration capacities of the absorbent.

$$\text{Cyclic capacity=rich loading (mol}_{gas}/\text{mol}_{amine})-\text{lean loading (mol}_{gas}/\text{mol}_{amine})$$ [Equation 2]

5. Chemical Reactions

The chemical absorption and separation reactions for $CO_2$, $H_2S$, and $CH_4$ using amine-based absorbents in the biogas absorption and regeneration process are shown in the following equations. When $CO_2$ is absorbed into the aqueous solution in the secondary amine absorbent, the main reactions take place as given in the following reaction formulas, where R is alkyl and R' is H for a primary amine and alkyl for a secondary amine.

<Carbamate Formation>

2RR'NH+CO$_2$↔RR'NH$_2$+$+$RR'NCOO$^-$ [Reaction Formula 1]

<Bicarbonate Formation>

CO$_2$+H$_2$O↔H$_2$CO$_3$ [Reaction Formula 2]

H$_2$CO$_3$↔HCO$_3^-$+H$^+$ [Reaction Formula 3]

CO$_2$+OH$^-$↔HCO$_3^-$ [Reaction Formula 4]

RR'NH$_2$+HCO$_3^-$↔[RR'NH$_2^+$][HCO$_3^-$] [Reaction Formula 5]

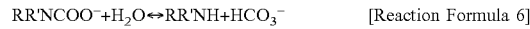
RR'NCOO$^-$+H$_2$O↔RR'NH+HCO$_3^-$ [Reaction Formula 6]

In addition to the formation of carbamate and bicarbonate, the zwitterion mechanism has been shown to form carbamate for primary and secondary amines, in which case it forms an intermediate mediator zwitterion (RR'NH+COO$^-$). The zwitterion reactions follow the reaction formulas:

CO$_2$+RR'NH↔RR'NH$^+$COO$^-$ [Reaction Formula 7]

RR'NH+COO$^-$+RR'NH↔RR'NCOO$^-$+RR'NH$_2$ [Reaction Formula 8]

The reaction between the tertiary amine-absorbent and $CO_2$ can be expressed as follows; it follows the Reaction Formula 9 without forming a carbamate, and MDEA in the tertiary amine is as given in the Reaction Formula 10.

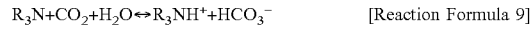
R$_3$N+CO$_2$+H$_2$O↔R$_3$NH$^+$+HCO$_3^-$ [Reaction Formula 9]

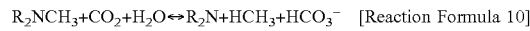
R$_2$NCH$_3$+CO$_2$+H$_2$O↔R$_2$N+HCH$_3$+HCO$_3^-$ [Reaction Formula 10]

AMP is a sterically hindered amine, reacts with $CO_2$ by the same reaction mechanism of the primary amine. For AMPs used as additives, they are expected to have the faster absorption rates than tertiary amines. PZ injected as an additive may react with the intermediate product, R'

(NHCOO)$_2$, generated by reacting with CO$_2$ as in the Reaction Formula 11 to rapidly react and regenerate as in the Reaction Formula 12, where R is (CH$_3$)$_2$CCH$_2$OH and R' is (CH$_2$)$_4$.

R'(NH)$_2$+2CO$_2$→R'(NHCOO)$_2$ [Reaction Formula 11]

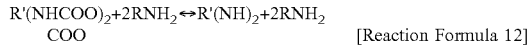

R'(NHCOO)$_2$+2RNH$_2$↔R'(NH)$_2$+2RNHCOO [Reaction Formula 12]

Therefore, it can be predicted that the addition of PZ accelerates the reaction and regeneration according to the Reaction Formulas 11 and 12. As described above, the effect of the interaction that can occur when MDEA is added to AMP through the reaction of amine-amine can be predicted as follows:

R$_2$NCH$_3$+CO$_2$↔R$_2$CH$_3$NCOO [Reaction Formula 13]

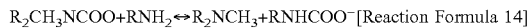

R$_2$CH$_3$NCOO+RNH$_2$↔R$_2$NCH$_3$+RNHCOO$^-$ [Reaction Formula 14]

In the absorption of hydrogen sulfide (H$_2$S) with the aqueous solution of primary and secondary amine-absorbents, the hydrogen sulfide (H$_2$S) dissociates as shown in the Reaction Formulas 15 and 16, where the main reaction is given as shown in the Reaction Formula 17.

H$_2$S↔H$^+$+HS$^-$ [Reaction Formula 15]

HS$^-$↔H$^+$+S$^-$ [Reaction Formula 16]

RR'NH+H$_2$S↔RR'NH$_2^+$+HS$^-$ [Reaction Formula 17]

Even in the tertiary amine-absorbent aqueous solution, the hydrogen sulfide (H$_2$S) participates in the reaction as follow:

R$_3$N+H$_2$S↔R$_3$NH$^+$+HS$^-$ [Reaction Formula 18]

6. Gas Selectivity

The selectivity coefficient tends to have a higher selectivity of the amine solvent for H$_2$S in the liquid phase than the H$_2$S/CO$_2$ content in the gas phase. Selectivity coefficients are based on H$_2$S selectivity. The value of the selectivity coefficient is equal to the ratio of H$_2$S/CO$_2$ in the liquid phase to H$_2$S/CO$_2$ in the gas phase.

$$S = \frac{x_{H2S}/x_{CO2}}{y_{H2S}/y_{CO2}}$$ [Equation 3]

The selectivity factor has no limit, and x is the mole fraction of component I in the liquid bulk.

Figure 3:
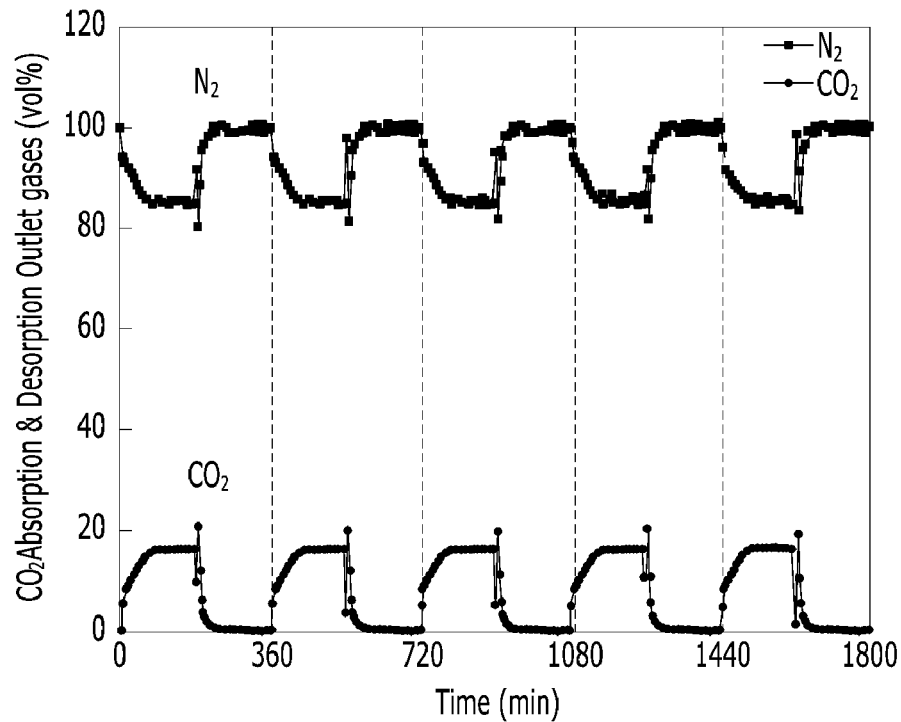
FIG. 3 is a graph showing the experimental results of 5-cycle absorption and regeneration of $CO_2$ (15 vol %) using an MDEA 5 wt % absorbent in accordance with an embodiment of the present invention.

7. Results and Discussion 7-1. Absorption and Regeneration of Single Gas and Mixed Gas In order to evaluate CO$_2$ absorption and regeneration capacity of bio byproduct gas, a single gas of acidic CO$_2$ and a mixed gas of CO$_2$+H$_2$S were independently absorbed and regenerated five times with an MDEA 5 wt % absorbent. A blended absorbent using additives was very reactive to increase the absorption capacity. Simultaneous absorption and regeneration of the single gas of CO$_2$ and the mixed gas of CO$_2$+H$_2$S were confirmed. FIG. 3 shows the results of GC analysis on the outlet gas in five experiments of CO$_2$ absorption and regeneration using an MDEA 5 wt % absorbent. Absorption and regeneration were confirmed using CO$_2$ (15 vol %) and N$_2$ balance gas. In five consecutive experiments under the same conditions of absorption and regeneration, CO$_2$ (15 vol %) absorption equilibrium and desorption equilibrium were identified.

Figure 4:
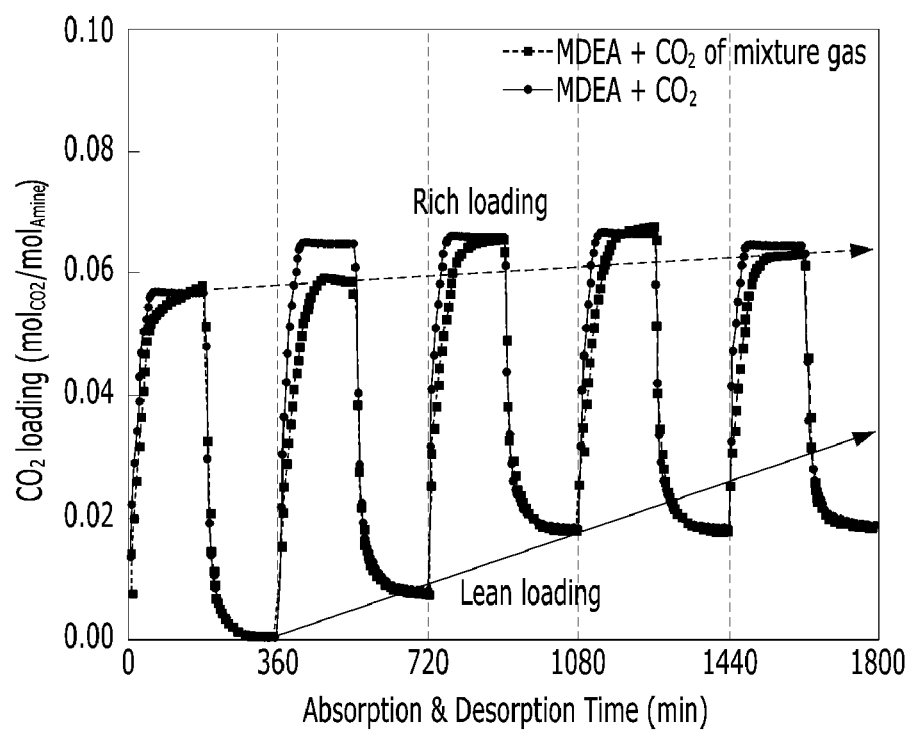
FIG. 4 is a graph showing the experimental results of absorption and regeneration of $CO_2$ (15 vol %) and a mixed gas of $CO_2$ (15 vol %) and $H_2S$ (50 ppm) using an MDEA 5 wt % absorbent in accordance with an embodiment of the present invention.

The MDEA 5 wt % absorbent was used to confirm the analytical results of CO$_2$ (15 vol %) and H$_2$S (50 ppm)+balance gas. The same trends were observed for the mixed gas of CO$_2$+H$_2$S and for the single gas of CO$_2$. FIG. 4 shows the results of five consecutive experiments of absorption and regeneration for the single gas of CO$_2$ and the mixed gas of CO$_2$ (15 vol %)+H$_2$S (50 ppm) using MDEA (5 wt %). At a constant absorption temperature of 35° C. and a constant regeneration temperature of 80° C., the rich loading value due to the absorption temperature had the same loading value, but the base line rose because complete regeneration was not achieved because of the low regeneration temperature. As a result of the regeneration temperature above three cycles, lean loading was constant. Rich loading was low because of evaporation of the absorbent and reduced performance of the absorbent. In comparison of the outlet gas analysis results, the trends of the single gas of CO$_2$ and the mixed gas of CO$_2$+H$_2$S were similar, but the absorption equilibrium was absorbed in the absorption experiment using MDEA 5 wt % absorbent of CO$_2$+H$_2$S mixed gas. Seems to reach a difference. When comparing the loading values of absorption and regeneration of the single gas of CO$_2$ (15 vol %) and the mixed gas of CO$_2$ (15 vol %)+H$_2$S (50 ppm), absorption and regeneration of CO$_2$ loading show the same loading values. In terms of absorption of the single CO$_2$ gas and the mixed gas, H$_2$S (50 ppm) had no effect on CO$_2$ (15 vol %).

7-2. Mixed Gas Absorption and Regeneration in MDEA

Figure 5:
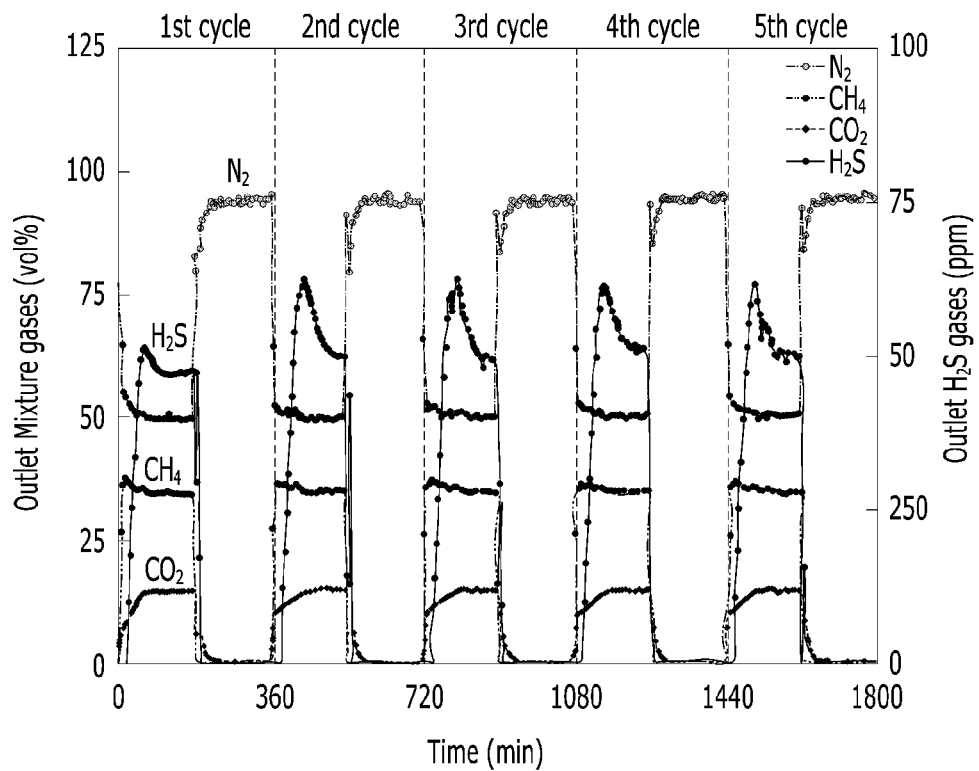
FIG. 5 is a graph showing the analytical results of 5-cycle absorption and regeneration of a mixed gas using an MDEA 5 wt % absorbent in accordance with an embodiment of the present invention.
Figure 6:
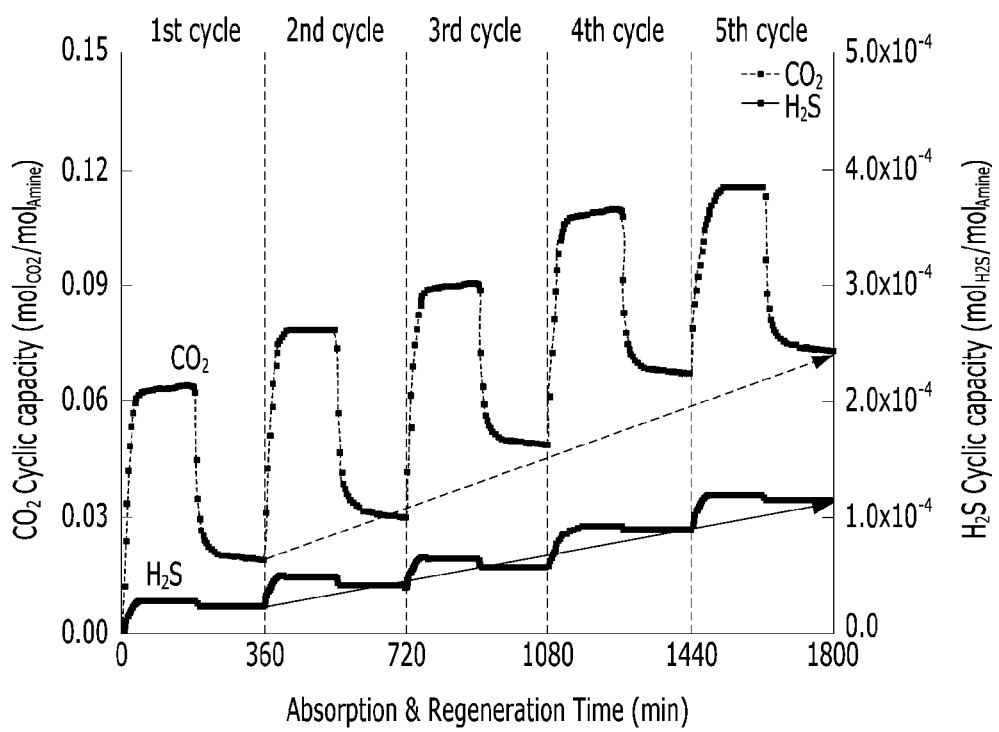
FIG. 6 is a graph showing the experimental results of 5-cycle absorption and regeneration using an MDEA 5 wt % absorbent and a mixed gas of $CO_2$ and $H_2S$ in accordance with an embodiment of the present invention.

Simultaneous absorption and regeneration experiments were carried out five times using a mixed gas of CO$_2$ (15 vol %), H$_2$S (50 ppm), CH$_4$ (35 vol %), and N$_2$ balance gas using MDEA 5 wt % absorbent. FIG. 5 shows the results of GC analysis on the outlet gas after treat gas. CO$_2$ and H$_2$S have solubility in absorbents and are absorbable and renewable. CH$_4$ and N$_2$ are not bound to amine absorbents. In the CO$_2$ (15 vol %) and H$_2$S (50 ppm) equilibrium states after absorption and regeneration, CH$_4$ (35 vol %) and N$_2$ were not absorbed and separated according to the analysis results. The solubility of H$_2$S was higher than that of CO$_2$ at a same temperature pressure, and it took more time to reach the absorption equilibrium of H$_2$S even after CO$_2$ absorption. The absorbent performance for the mixed gas showed the same trend five times. FIG. 6 shows the results of five consecutive absorption and regeneration experiments for the mixed gas using an MDEA 5 wt % absorbent. Because of the difference between rich loading and lean loading of CO$_2$, cyclic capacity was 0.04 mol$_{CO2}$/mol$_{amine}$. Because of incomplete regeneration at relatively low regeneration temperatures of 80° C., the base line for lean loading became increasingly higher. At the same time, H$_2$S was also absorbable and renewable. H$_2$S also had the higher the baseline because of incomplete regeneration at 80° C. Cyclic capacity was confirmed through simultaneous absorption and regeneration of CO$_2$ and H$_2$S in the mixed gas.

7-3. Mixed Gas Absorption and Regeneration in MDEA+PZ

Figure 7:
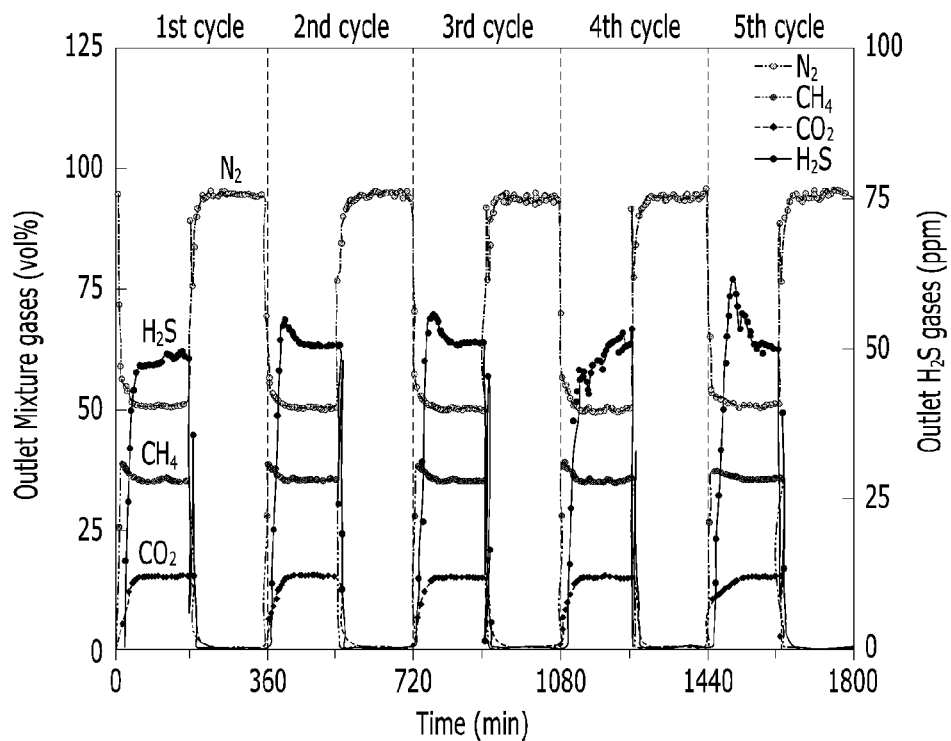
FIG. 7 is a graph showing the experimental results of 5-cycle absorption and regeneration of a mixed gas using an MDEA 4.5 wt %+PZ 0.5 wt % absorbent in accordance with an embodiment of the present invention.

Five times of absorption and regeneration experiments were carried out using N$_2$ balance gas to compare the continuous absorption and regeneration for CO$_2$ and H$_2$S with MDEA 5 wt % and for CO$_2$ (15 vol %), H$_2$S (50 ppm) and CH$_4$ (35 vol %) with MDEA 4.5 wt %/PZ 0.5 wt %. FIG. 7 is the GC analysis of the outlet gas after treatment. Absorption equilibrium and regeneration equilibrium were confirmed using a gas having the same composition of the MDEA 5 wt % absorbent. Absorption of the mixed gas of CO$_2$ (15 vol %) and H$_2$S (50 ppm) was confirmed by an equilibrium analysis. CH$_4$ and N$_2$ were not absorbed into the absorbent, but separated from the absorbent (Refer to FIG. 8). The same procedures were performed with the MDEA/PZ absorbent to compare the MDEA 5 wt % absorbent with the MDEA/PZ absorbent, confirming that the same absorption regeneration occurred continuously. As a result of analysis, MDEA/PZ showed a high $CO_2$ cyclic capacity of 0.01 $mol_{CO2}/mol_{amine}$ but low loading of $H_2S$. Compared with MDEA 5 wt %, MDEA/PZ resulted in the higher absorption performance and the far lower regeneration performance, which was based on the base line. This was due to the difference in the absorbent capacity, and there appeared no difference in the absorption performance depending on the difference of the regeneration temperature of the absorbent. Yet it was found that the $CO_2$ absorption and regeneration performance of a single amine absorbent or a mixed amine absorbent were different in low absorbents.

Figure 9:
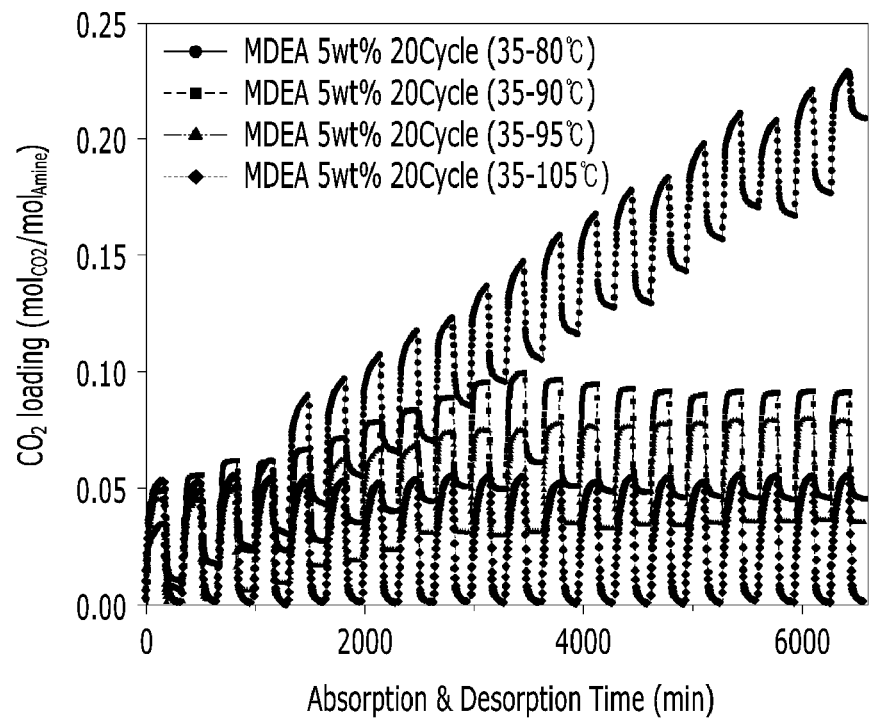
FIG. 9 is a graph showing the experimental results of 20-cycle $CO_2$ absorption and regeneration using a MDEA 5 wt % absorbent as a function of the regeneration temperature in accordance with an embodiment of the present invention.

As for desorption rate, it was important how easy desorption from the loading amine was. In order to confirm the regeneration performance depending on the absorption temperature, as shown in FIG. 9, a single gas of $CO_2$ was absorbed with the MDEA 5 wt % absorbent at 35° C. continuously for 20 cycles and regenerated at 80, 90, 95, and 105° C. The lean loading part continuously rose because of the complete regeneration at 80° C., and regeneration equilibrium occurred after the 10th cycle due to incomplete regeneration at 90° C. and 95° C. This confirmed the absorption performance of the absorbent for 20 cycles of absorption and regeneration. For smooth regeneration, it was necessary to maintain the regeneration temperature above 100° C. because of the influence of water, the chief constituent of the absorbent.

Figure 8:
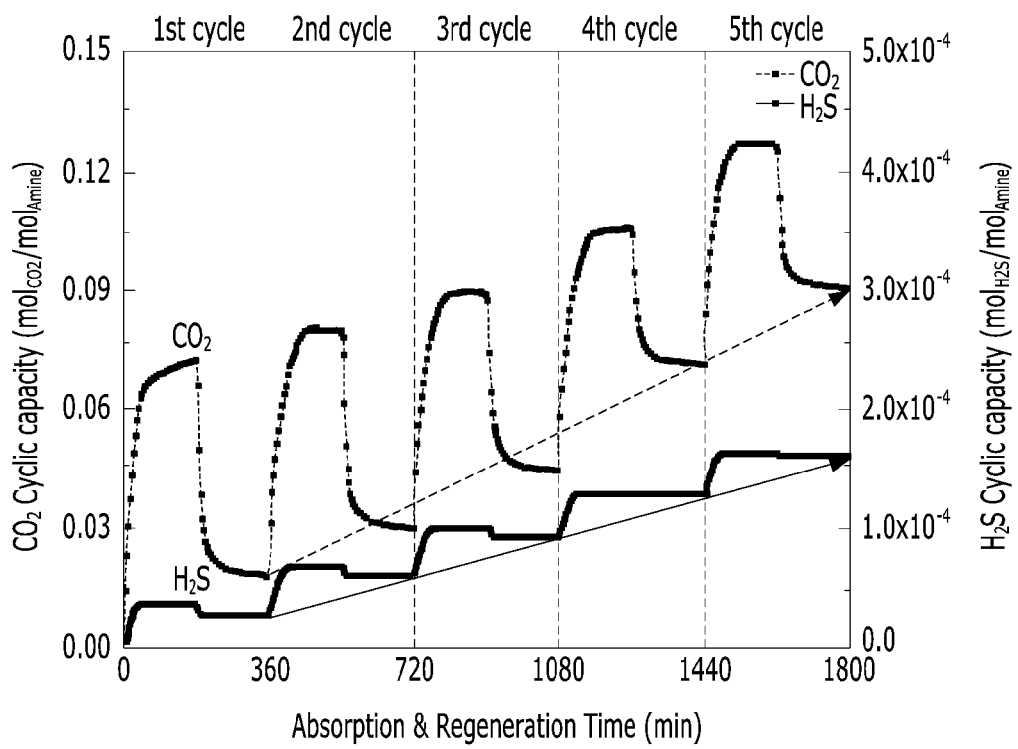
FIG. 8 is a graph showing the experimental results of 5-cycle absorption and regeneration using an MDEA 4.5 wt %+PZ 0.5 wt % absorbent and a mixed gas of $CO_2$ and $H_2S$ in accordance with one embodiment of the present invention.

As shown in FIGS. 4 and 6, the baseline of lean loading increased because a complete regeneration of the absorbent was impossible. FIGS. 8 and 9 show that the base line for lean loading increased due to incomplete regeneration. Incomplete regeneration at temperatures below 100° C. also increased the base line, and regeneration completed at temperatures above 105° C. Absorption occurred without complete regeneration; the baseline gradually increased with the continuous progress of the absorption and regeneration, but became constant due to the performance of the absorbent. As the absorbent had a low concentration, complete regeneration was achieved. The regeneration experiments carried out at that temperature were intended to explain the incomplete or complete regeneration achieved.

7-4. Absorption and Regeneration Using Mixed Gas of MDEA+Additive

What follows are the results of the absorption and regeneration experiments for $CO_2$ (15 vol %) and $H_2S$ (50 ppm) using a blended absorbent of MDEA 4.5 wt %+additive 0.5 wt % varied with 12 different additives. A comparison of absorption and regeneration rates was also made, which was an important factor reflecting the reactivity of each amine system or blend.

(1) $CO_2$ Absorption and Desorption

Figure 10:
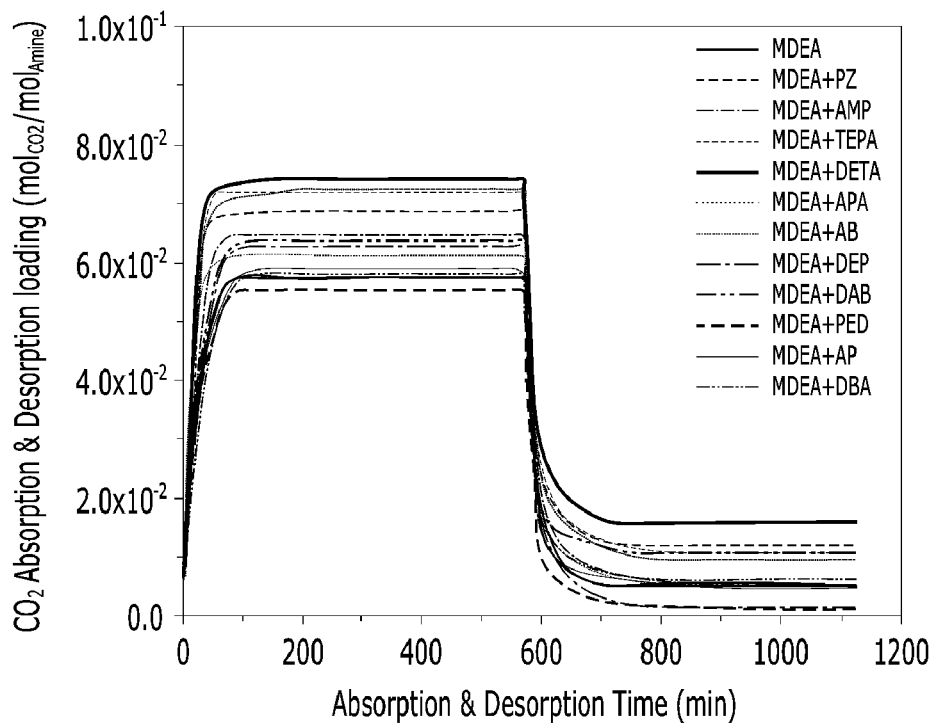
FIG. 10 is a graph showing the $CO_2$ cyclic capacity in a mixed gas using blended absorbents of MDEA+additive in accordance with an embodiment of the present invention.

Simultaneous absorption was performed for a mixed gas of $CO_2$ (15 vol %) and $H_2S$ (50 ppm) using a blended absorbent of MDEA+additive. FIG. 10 shows the results of $CO_2$ absorption and regeneration using blended absorbents of MDEA+additive with time. The $CO_2$ absorption and regeneration performance by the characteristics of the blended amine were compared, and the absorption rate and regeneration rate were determined. The higher the absorption rate and the regeneration rate, the better the loading value.

Figure 11:
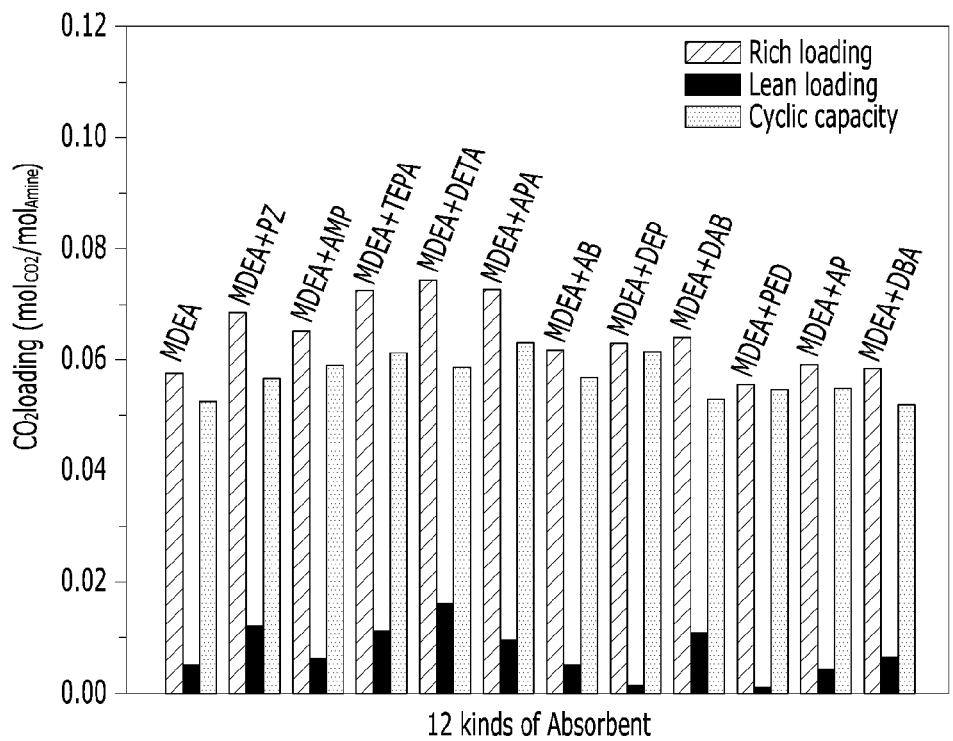
FIG. 11 is a graph showing the cyclic capacity as a function of $CO_2$ rich loading and lean loading for each absorbent in a mixed gas in accordance with an embodiment of the present invention.

FIG. 11 shows the rich loading, lean loading, and cyclic loading of each additive for selecting absorbents with excellent $CO_2$ absorption and regeneration performances in the mixed gas. $CO_2$ rich loading by blended absorbents was excellent in DETA, TEPA, APA, PZ, and AMP. The blended absorbent enhanced the reactivity as an activator of the MDEA absorption capacity by the shuttle effect. As a result of $CO_2$ rich loading for each additive, DETA, TEPA, and APA were secondary amines. MDEA/PZ, a commercial absorbent, showed higher $CO_2$ absorption than MDEA, and $CO_2$ rich loading was also an excellent sterically hindered amine in AMP. Additives with good circulation capacity of $CO_2$ absorption and regeneration according to additives of absorbents using a mixture of $CO_2$ and $H_2S$ are represented as follows: APA>DEP>TEPA>AMP>DETA>AB>PZ>AP>PED>DAB>MDEA>DBA. As experimental results, the additive was excellent as an active agent, but PED displayed its performance as a $CO_2$ absorbent additive. DEP and PED showed a low lean loading, but APA had the highest cyclic capacity due to the difference in the absorption and regeneration results.

(2) $H_2S$ Absorption and Desorption

Figure 12:
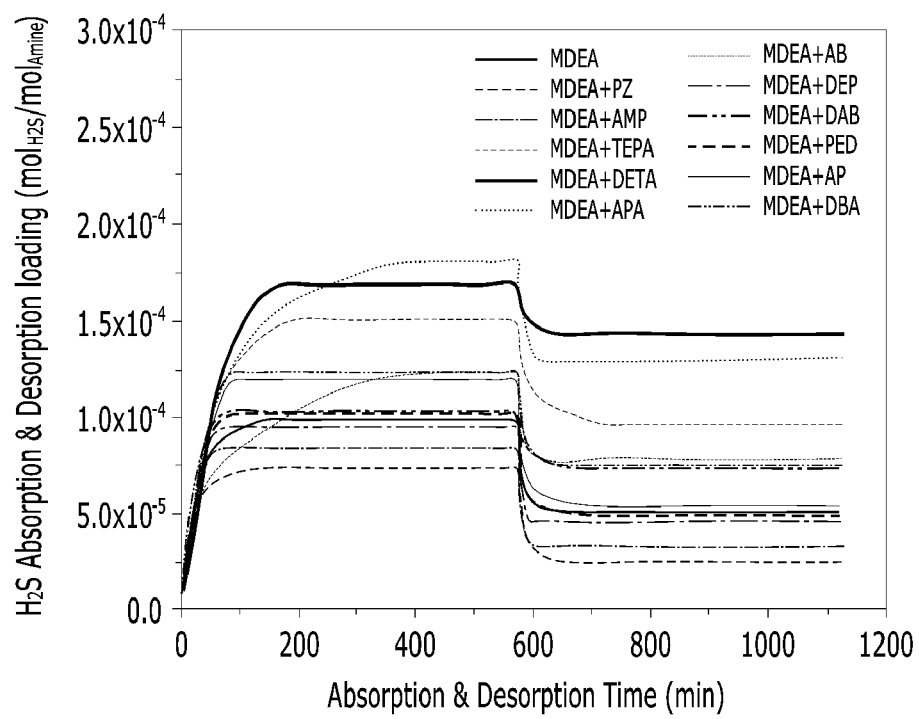
FIG. 12 is a graph showing the $H_2S$ cyclic capacity in a mixed gas using blended absorbents of MDEA and additive in accordance with an embodiment of the present invention.

Simultaneous absorption was performed using a mixed gas of $CO_2$ (15 vol %) and $H_2S$ (50 ppm) and blended absorbents of MDEA+additive. FIG. 12 shows the results of $H_2S$ absorption and regeneration using blended absorbents of MDEA+additive with time. Simultaneous absorption and regeneration experiments showed that $CO_2$ (15 vol %) and $H_2S$ (50 ppm) were simultaneously absorbed. $H_2S$ had a long absorption time unlike $CO_2$. In the case of $H_2S$, despite its high solubility in water, the loading value varied depending on the additive under the same conditions. DEP, AMP, and PZ based on MDEA 5 wt % showed higher $CO_2$ absorption capacity than MDEA 5 wt %, while $H_2S$ absorption was lower.

Figure 13:
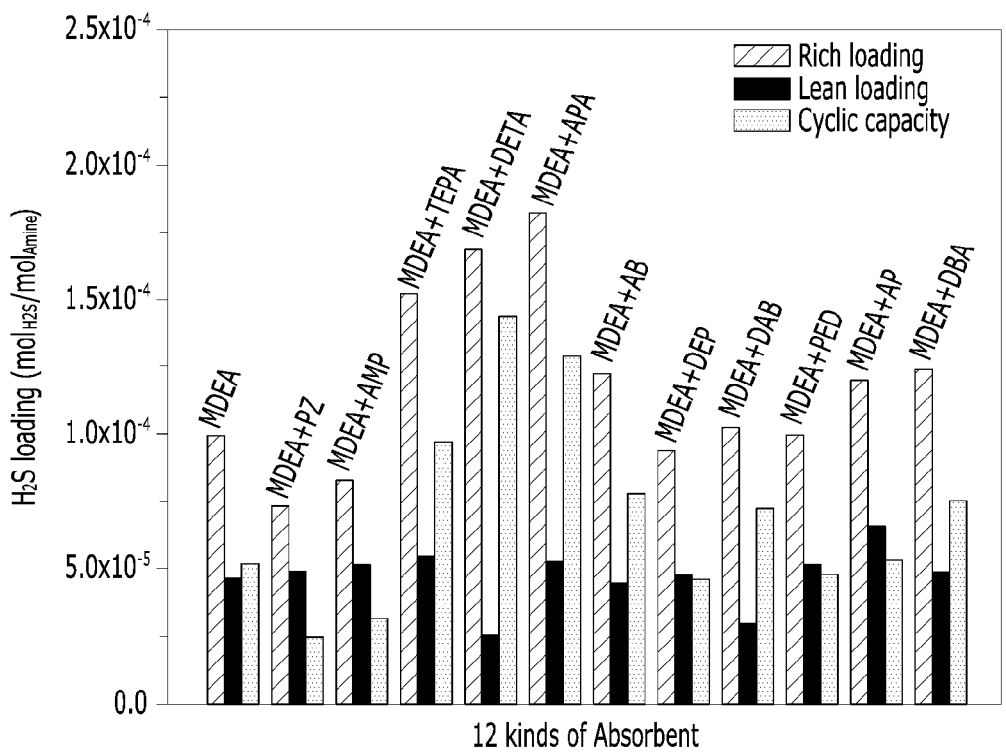
FIG. 13 is a graph showing the cyclic capacity as a function of $H_2S$ rich loading and lean loading for each absorbent in a mixed gas in accordance with an embodiment of the present invention.

FIG. 13 shows the rich loading, lean loading, and cyclic loading of each additive for selecting absorbents with good absorption and regeneration of $H_2S$ in the mixed gas. TEPA, DETA, and APA with excellent $CO_2$ absorption capacity showed higher $H_2S$ absorption loading values in the order of APA>DETA>TEPA. However, PZ and AMP, which have high $CO_2$ absorption capacity, have low $H_2S$ absorption capacity. Additives with good circulating capacity of $H_2S$ absorption and regeneration according to additives of absorbents using a mixture of $CO_2$ and $H_2S$ are expressed as follows: DETA>APA>TEPA>AB>DBA>DAB>AP>MDEA>PED>DEP>AMP>PZ. As shown in FIG. 13, APA additive showed the highest rich loading. DETA and DAB had the lowest lean loading. Therefore, DETA showed the highest circulation capacity. The additives of APA, DETA, and TEPA were relatively low in $CO_2$ absorption performance such as PZ and AMP, and anti-$H_2S$ bonding was expected to interfere with the formation of carbamate and bicarbonate formed by the reaction with $CO_2$. This can be seen from the results of absorption and regeneration of a single gas of $CO_2$ or $H_2S$ and selective absorption in the mixed gas.

Figure 14:
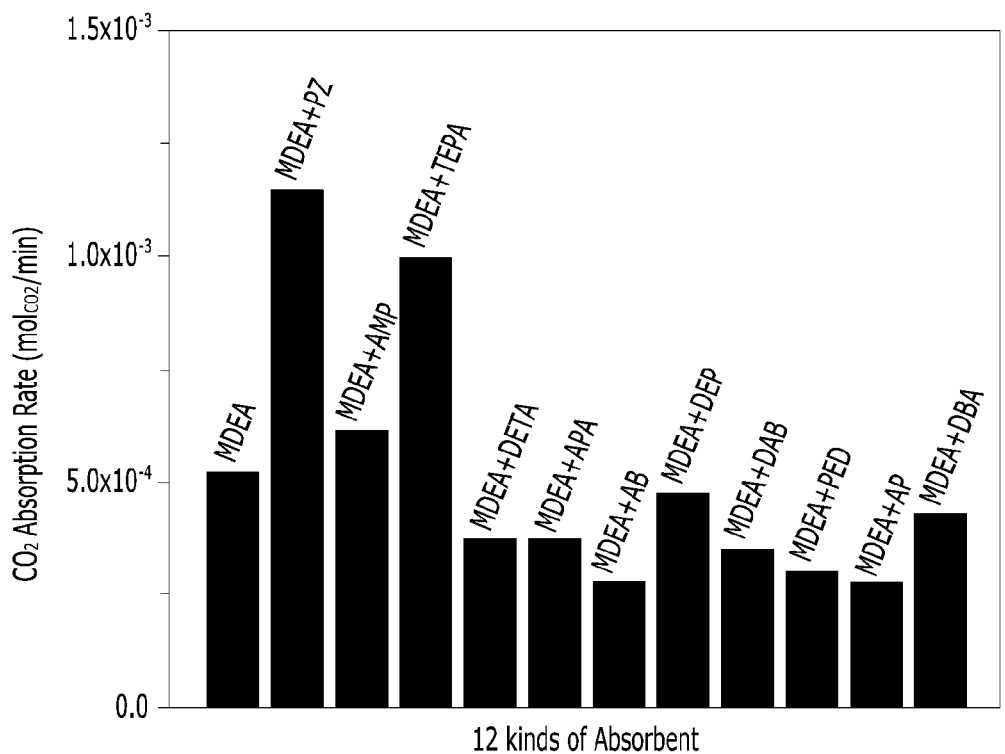
FIG. 14 is a graph showing the $CO_2$ absorption rate by absorbents in a mixed gas in accordance with an embodiment of the present invention.

7-5. Absorption and Regeneration Rates for $CO_2$ and $H_2S$ Using MDEA+Additive (1) $CO_2$ Absorption and Desorption Rates Using Mixed Gas The absorption rate and the regeneration rate are important in regards to contact time and energy, as well as the loading capacity of the additive-specific absorbent of which the primary absorbent is MDEA. FIG. 14 shows that PZ was most absorbed per hour, and AMP and TEPA were also superior to MDEA in the apparent velocity of each absorbent using the mixed gas. Although having higher $CO_2$ loading than MDEA, but all the additives except PZ, TEPA and AMP showed low apparent absorption rates.

Figure 15:
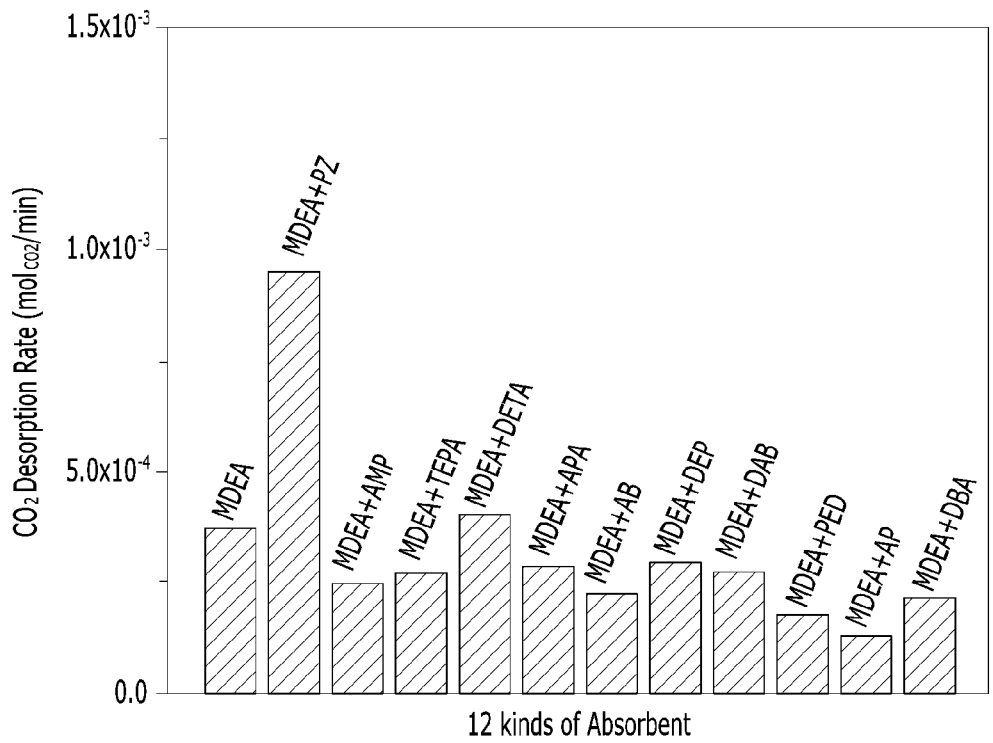
FIG. 15 is a graph showing the $CO_2$ regeneration rate by absorbents in a mixed gas in accordance with an embodiment of the present invention.

The regeneration rate of the absorbent is an important factor for the regenerative heat energy. This is because the lean loading from the continuous circulation process is recycled to the absorption tower. FIG. 15 shows the apparent regeneration rate of loaded $CO_2$ by additives. PZ, which had a high absorption rate, displayed excellent regeneration performance at 80° C. in relation to other additives. With the formation of the carbamate, the $CO_2$ desorption rate was high as a result of the high absorption rate.

(2) $H_2S$ Absorption and Desorption Rate Using Mixed Gas

Figure 16:
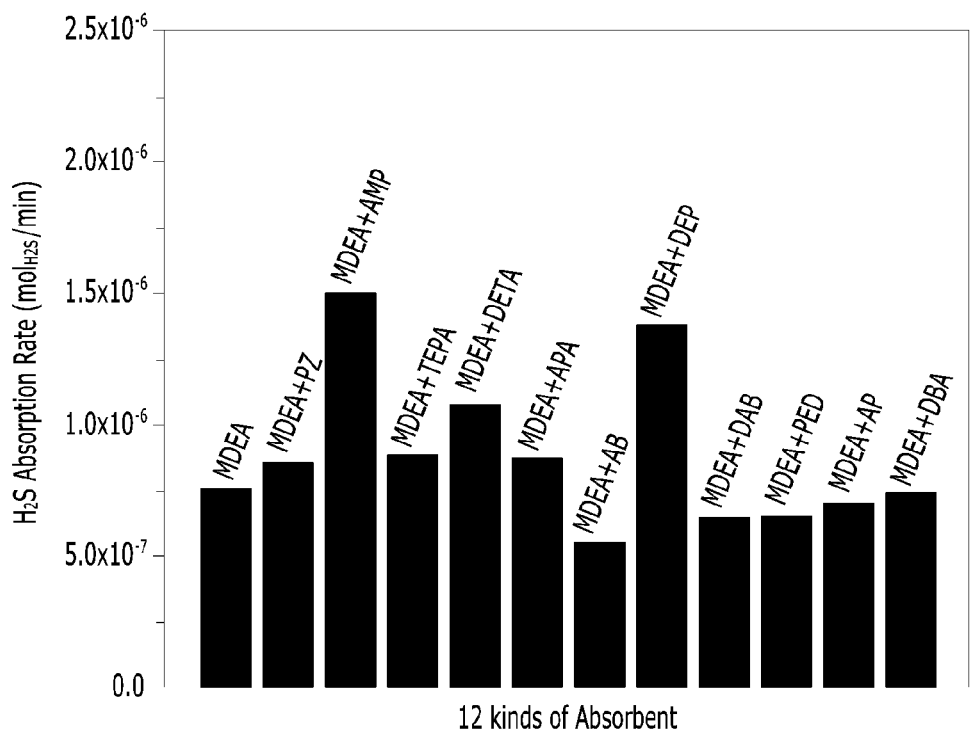
FIG. 16 is a graph showing the $H_2S$ absorption rate by absorbents in a mixed gas in accordance with an embodiment of the present invention.

The simultaneous absorption and regeneration rate of $H_2S$ in the mixed gas was compared for each additive. FIG. 16 shows the absorption rate of $H_2S$ in mixed gas. Additives AMP and DEP showed lower $H_2S$ absorption capacity than an MDEA-only absorbent, but the absorption rate was faster. Additives TEPA, DETA, and APA showed high absorption capacity at the same time, but the absorption rate was similar to that of MDEA.

Figure 17:
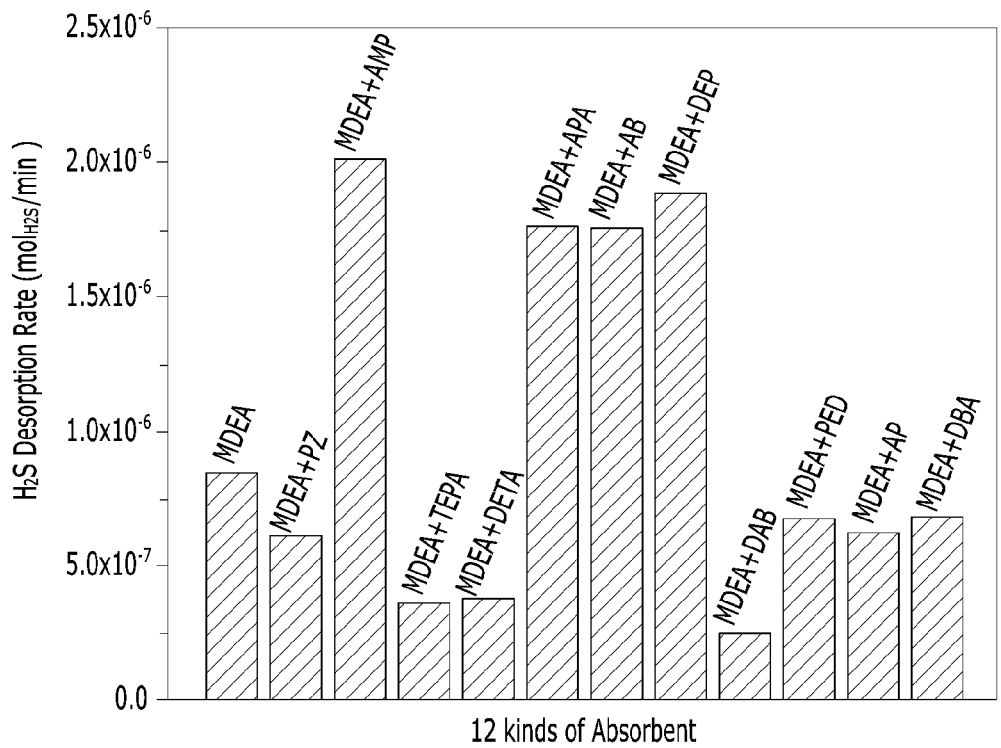
FIG. 17 is a graph showing the $H_2S$ regeneration rate by absorbents in a mixed gas in accordance with an embodiment of the present invention.
Figure 18:
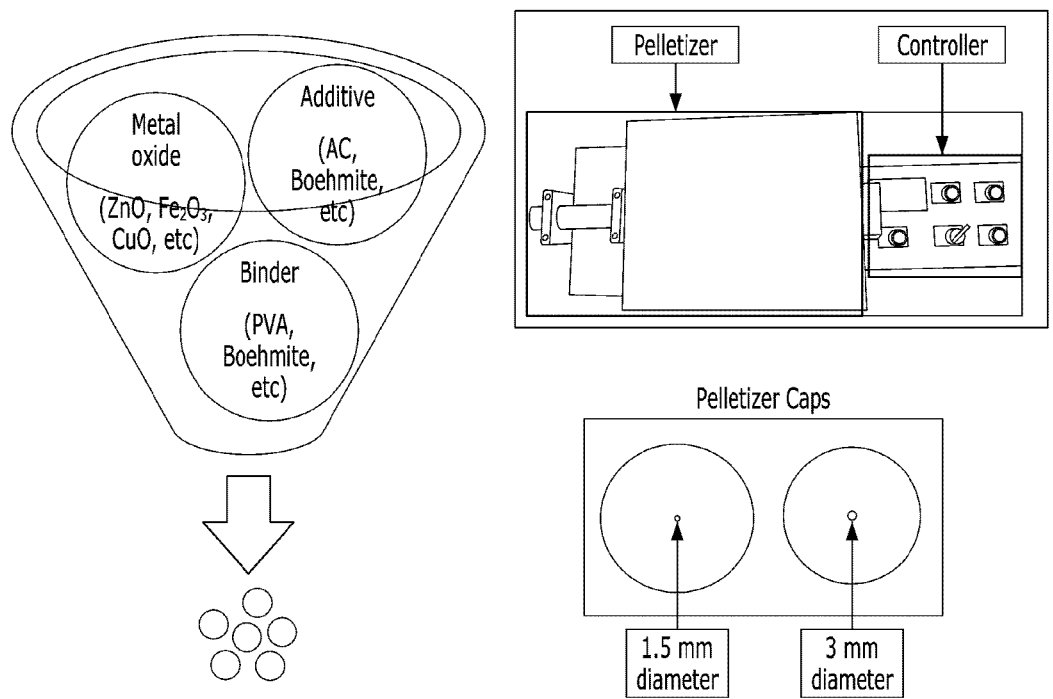
FIG. 18 shows a cylindrical pelletizer used in the manufacturing method of the $H_2S$ adsorbents in accordance with an embodiment of the present invention.

FIG. 17 shows the regeneration rate of $H_2S$ by absorbent additive in the mixed gas. AMP, APA, AB, and DEP showed faster regeneration performance than the MDEA-only absorbent, which was different from the $CO_2$ regeneration rate.

8. Conclusions

Simultaneous absorption of $CO_2$ and $H_2S$ was carried out using MDEA blended with 12 different additives. As an alternative to commercial absorbents of MDEA/PZ mixture, optimal absorbents with excellent loading values were selected from a comparison of measurements of regeneration efficiency, absorption rate, and regeneration rate using low energy.

The $CO_2$ absorption capacity of the mixed gas was highest with the MDEA/DETA among the absorbents, but the circulation capacity was highest with the MDEA/APA. The $H_2S$ absorption capacity was highest with MDEA/APA, but the cyclic capacity was highest with MDEA/DETA.

The apparent absorption rate of $CO_2$ in mixed gas was highest with MDEA/PZ, and also, the apparent regeneration rate was highest in the MDEA/PZ. The apparent absorption rate of $H_2S$ was highest with MDEA/AMP and also the apparent regeneration rate was highest with MDEA/AMP.

MDEA/PZ and MDEA/AMP were superior in the apparent absorption rate and the apparent regeneration rate in $CO_2$ and $H_2S$, respectively. This indicates that the combination of PZ or AMP with acid gas showed excellent desorption performance for structural reasons.

4.5 wt % of MDEA was mixed with 0.5 wt % of additives. MDEA/TEPA and MDEA/DETA had high loading values because of the large number of amino groups, but MDEA/APA-mixed absorbents having three amine groups showed excellent performance in terms of the simultaneous absorption capacity for $CO_2$ and $H_2S$. This study confirmed from the continuous experiments that the MDEA/APA was superior as an alternative absorbent in the $CO_2$ absorption and regeneration capacity and can be reused as an absorbent excellent in absorption and regeneration of $H_2S$ and $CO_2$.

Example 2. $H_2S$ Separation Using Metal Oxide Adsorbent

1. Experiment Method

Figure 19:
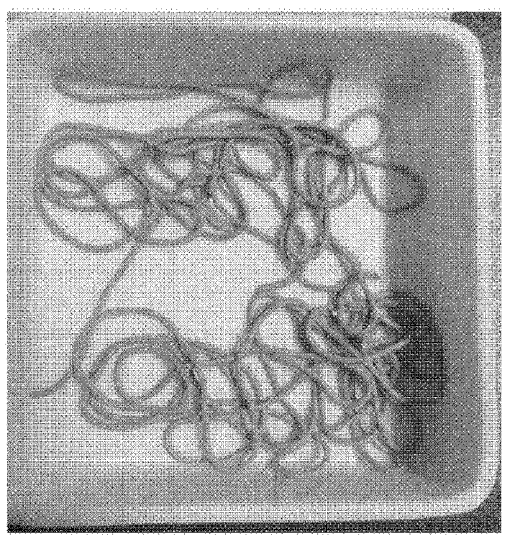
FIG. 19 is a photographic image of a pellet-shaped adsorbent in accordance with an embodiment of the present invention.
Figure 19:
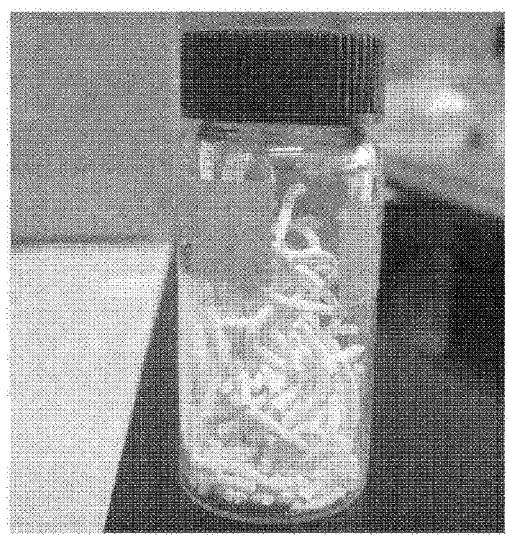

In order to perform high-grade $H_2S$ treatment with adsorbents of the present invention, metal oxides (ZnO, $Fe_2O_3$, CuO, etc.) and a binder (AC, boehmite, PVA) were used as basic materials to prepare adsorbents for separation of $H_2S$ in a biogas. For an $H_2S$ removal in the biogas using a fixed-bed reactor, an adsorbent easy to place in the reactor was prepared. The adsorbent was prepared in the cylinder form as shown in FIG. 19, and its preparation process consisted of mixing a metal oxide and a binder into slurry and injecting the slurry into a pelletizer. The cylinder-shaped adsorbent (hereinafter, referred to as "pellet") was formed to have a diameter of 1.5 mm or 3 mm with a yield of 200 g per production cycle. At the completion of pelletization, the adsorbent was subjected to plastic molding at 850° C. for 5 hours.

Figure 20:
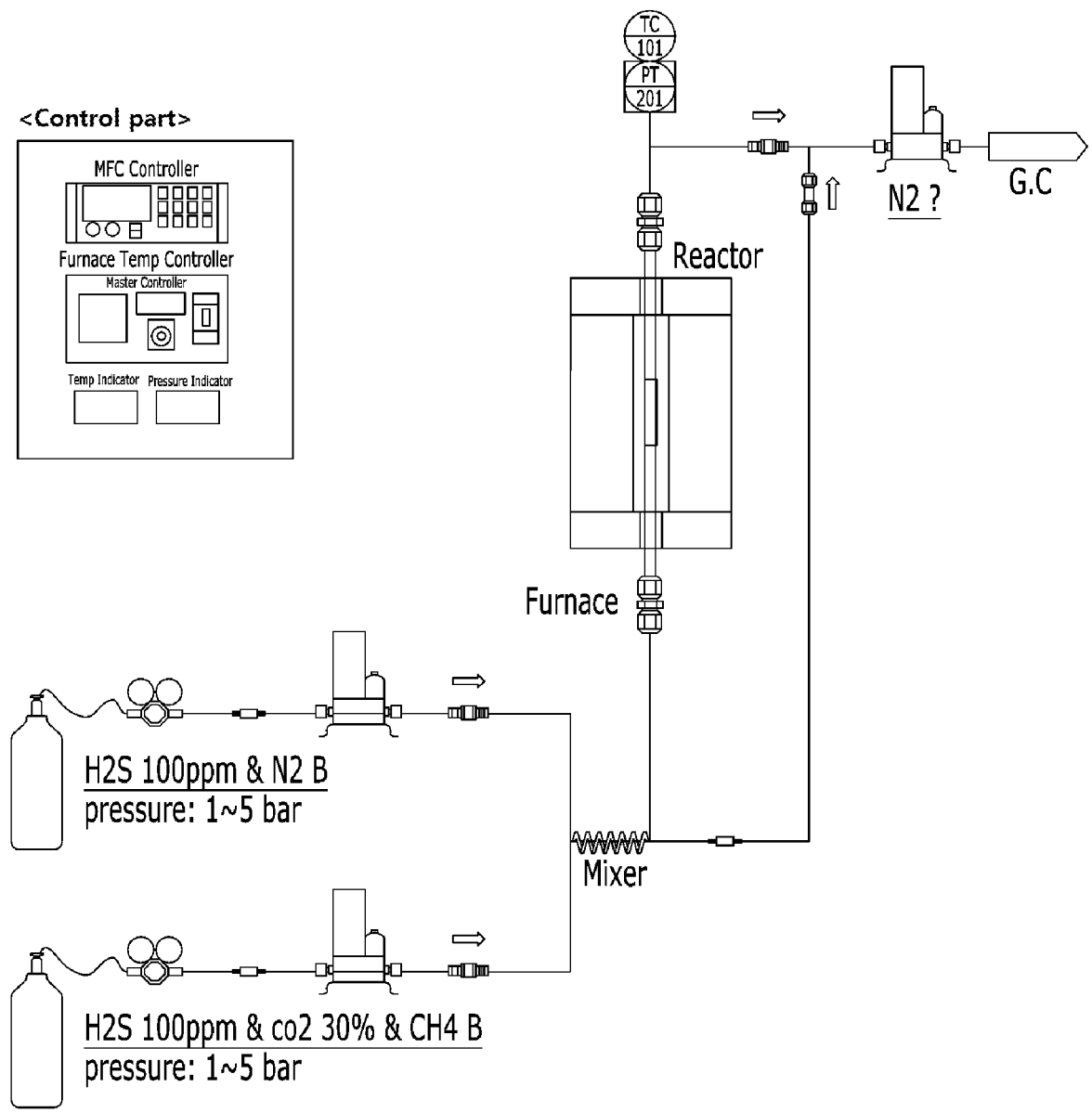
FIG. 20 is a schematic diagram of an apparatus for evaluating the adsorption capacity of $H_2S$ adsorbents in accordance with an embodiment of the present invention.

An apparatus for adsorbent performance evaluation was constructed with a fixed-bed reactor, a reactor control, and an analyzer, as shown in FIG. 20. Using the fixed-bed reactor with glass fiber filled in the bottom and 3 g of the adsorbent placed on the top, the experimental procedures were carried out to measure the concentration of hydrogen sulfide ($H_2S$) for breakthrough curve analysis. The $H_2S$ breakthrough curve analysis using a fixed-bed reactor was conducted under the conditions of temperature 25° C., pressure 1.4 bar, filling adsorbent 3 g (bulk density: 0.48 g/cm$^3$), model gas flow 100 cc/min, and model gas concentration 100 ppm ($H_2S$ balanced with $N_2$).

2. Experimental Results

The $H_2S$ adsorption capacity of the pelleted adsorbents according to the present invention was determined using three calculation methods (Chem. Eng. Journal, 304, p399-407, 2016).

2-1. ZnO-Based Adsorbents

Figure 21A:
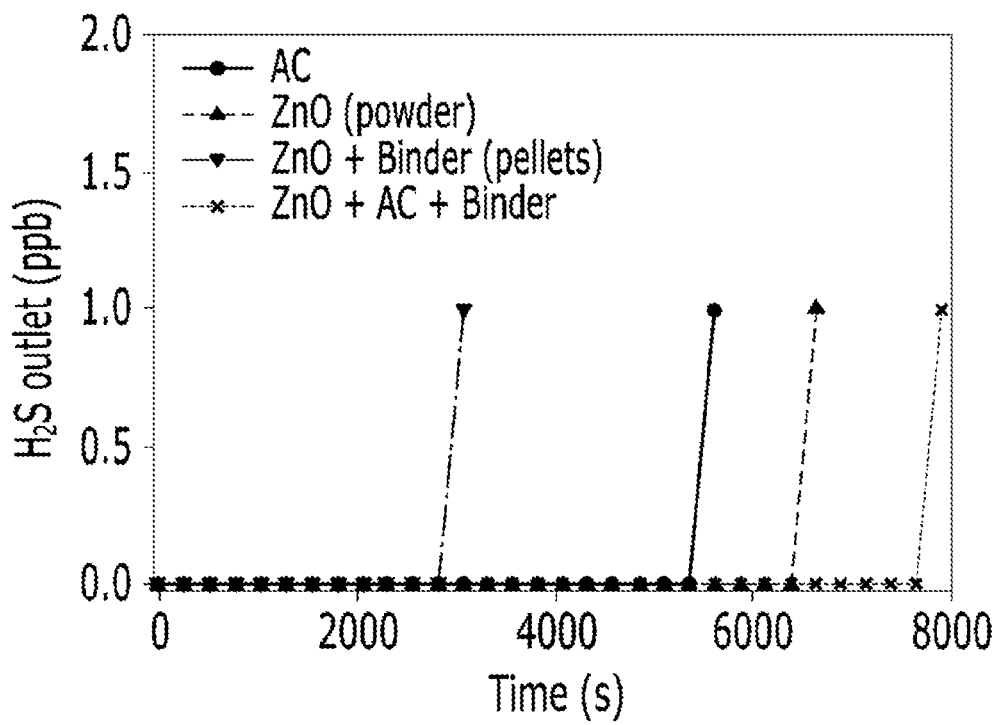
FIG. 21a, FIG. 21b and FIG. 21c present the results of performance evaluation of ZnO-AC composite adsorbents in accordance with an embodiment of the present invention.
Figure 21B:
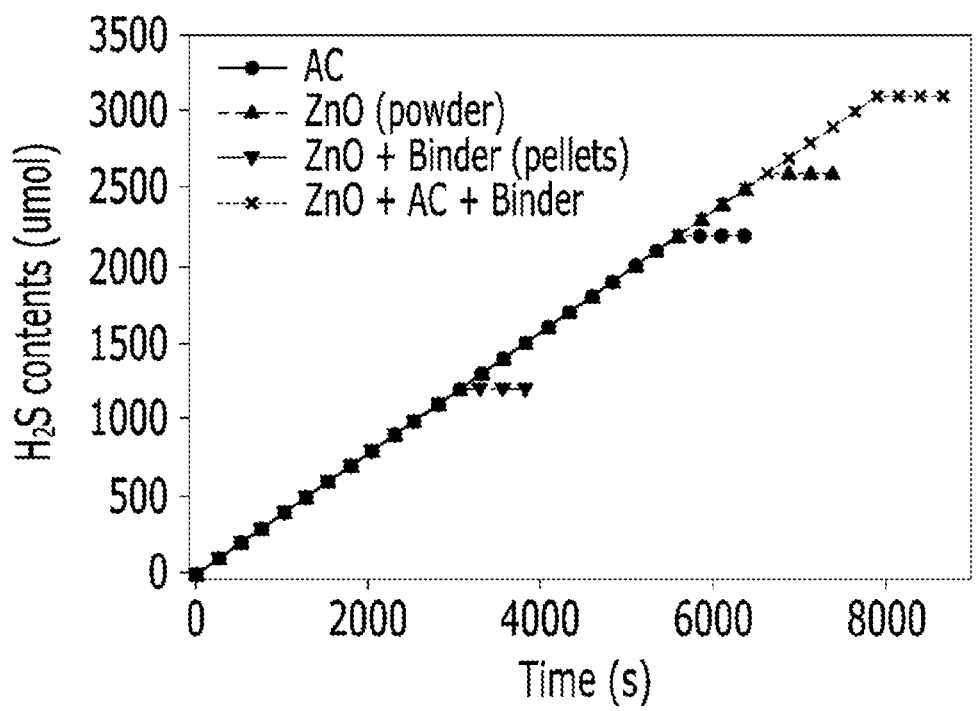
Figure 21C:
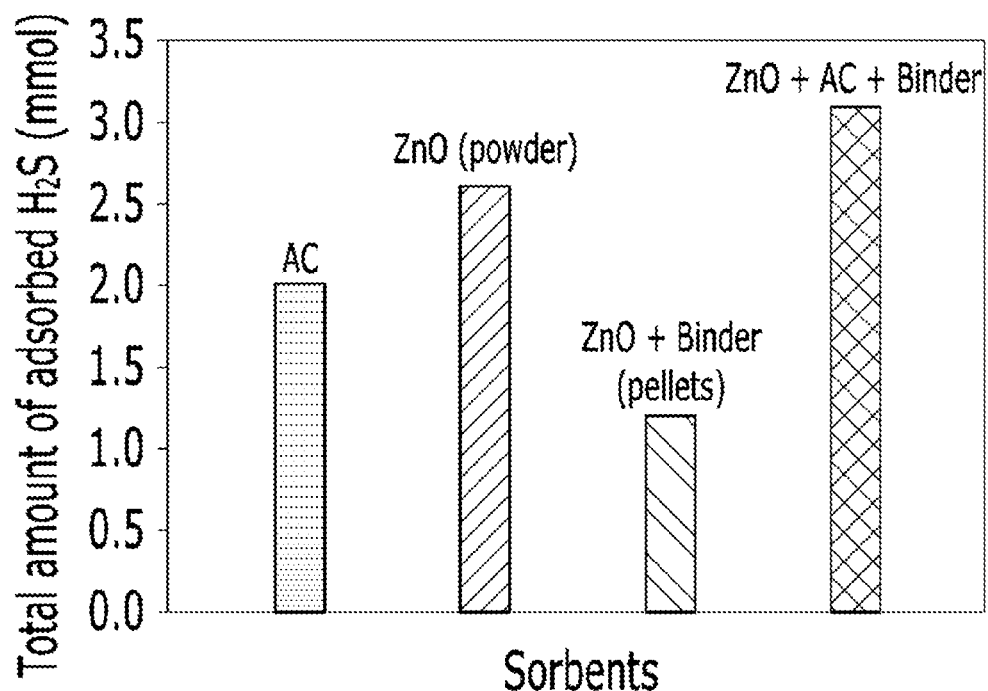

FIG. 21a, FIG. 21b and FIG. 21c show the $H_2S$ adsorption capacity of ZnO-based adsorbents containing activated carbon (AC) and polyvinyl alcohol (PVA, binder): (FIG. 21a) breakthrough curves; (FIG. 21b) the amount of adsorbed $H_2S$; and (FIG. 21c) the total amount of adsorbed $H_2S$ by the adsorbents. It can be seen from the breakthrough curve that a complete adsorption of $H_2S$ was achieved for a defined period of time. The specific surface area was 10.98 m$^2$/g for the ZnO pellet and 35.72 m$^2$/g for the ZnO-AC pellet. The trend of the $H_2S$ breakthrough curve appeared in the order of ZnO pellet <AC<ZnO powder <ZnO-AC pellet. The breakthrough time for 3 g of the ZnO-AC pellet was 7,900 sec (2.19 hour). The total amount of adsorbed $H_2S$ on the adsorbents based on metal oxide ZnO and a binder AC according to the present invention was 1.3 mmol for ZnO pellet, 2.2 mmol for AC pellet, 2.8 mmol for ZnO powder, and 3.2 mmol for ZnO-AC composite pellet. It was implied that an addition of the activated carbon (AC) contributed to increasing the specific surface area of the adsorbents and hence enhanced the $H_2S$ adsorption capacity.

Figure 22A:
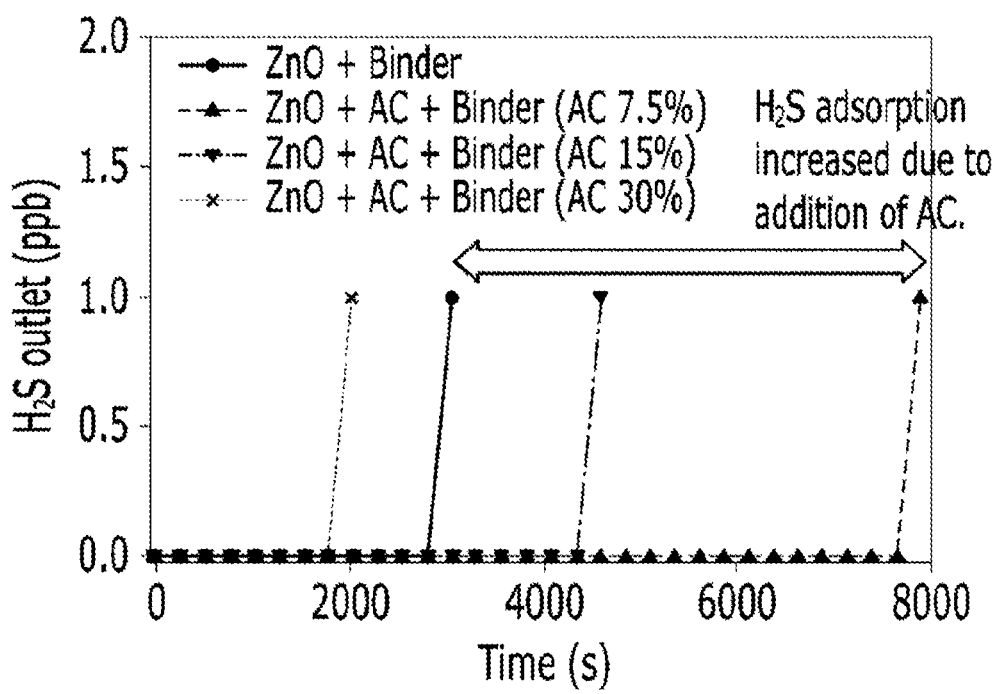
FIG. 22a, FIG. 22b and FIG. 22c present the results of performance evaluation of ZnO-AC composite adsorbents as a function of the contents of ZnO and AC in accordance with an embodiment of the present invention.
Figure 22B:
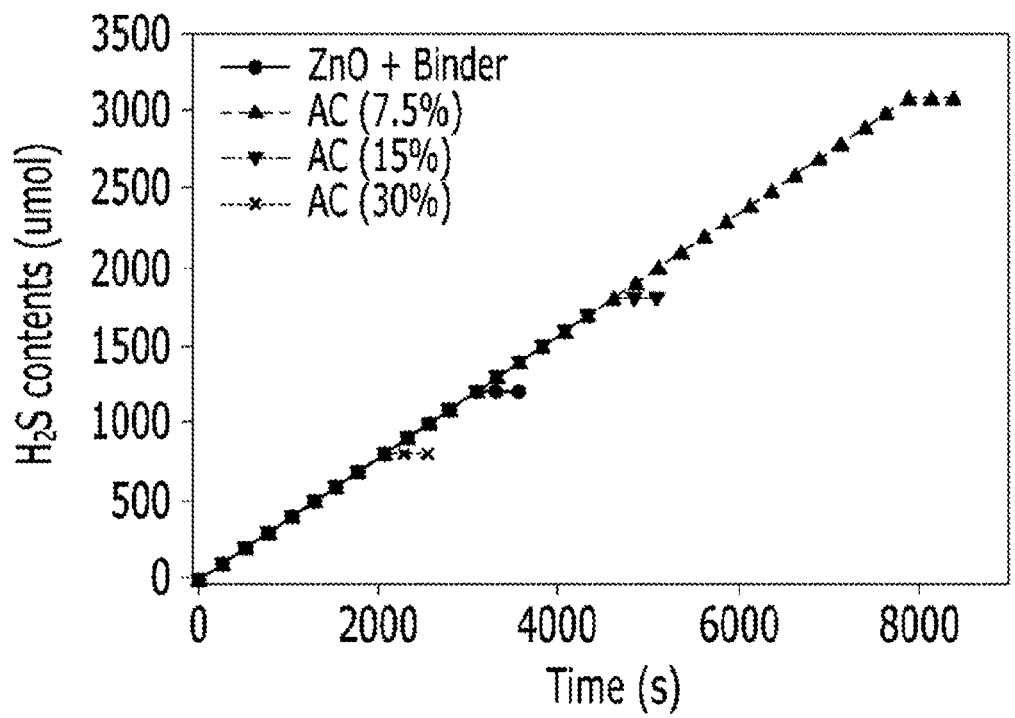
Figure 22C:
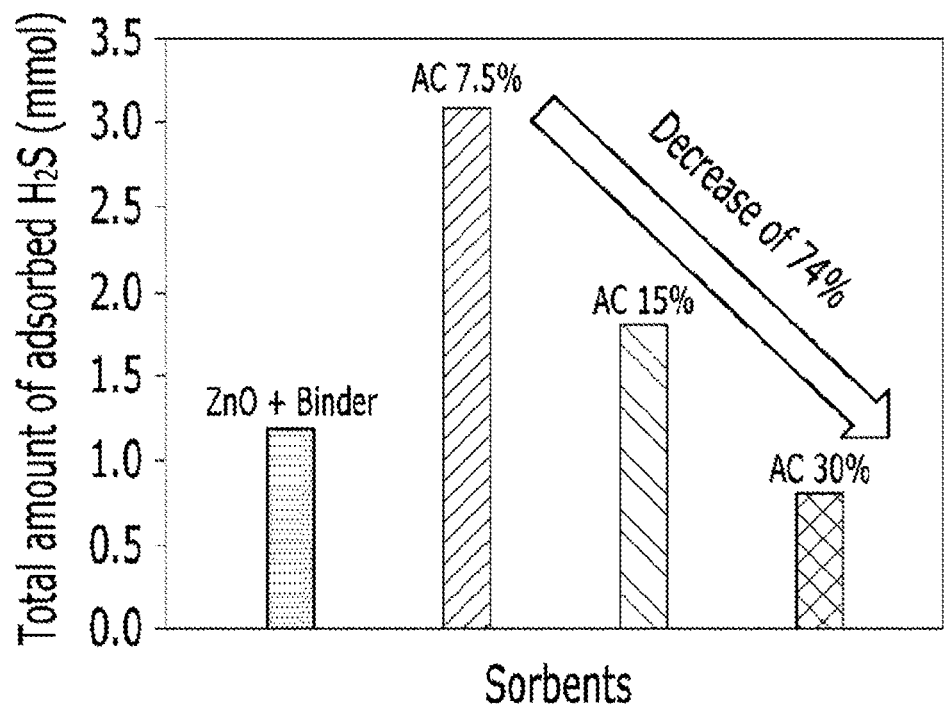

FIG. 22a, FIG. 22b and FIG. 22c shows the $H_2S$ adsorption capacity of ZnO-AC adsorbents containing metal oxide of ZnO and activated carbon (AC), as a function of the AC content: (FIG. 22a) breakthrough curves; and (FIG. 22b) and (FIG. 22c) the amount of adsorbed $H_2S$. The adsorption capacity decreased with an increase in the AC content from 7.5% to 15% and 30%. Particularly, the adsorption capacity with the AC content of 30% was lower than that with the AC content of zero. As for the amount of adsorbed $H_2S$ as a function of the AC content, the adsorbent having the AC content of 7.5% with ZnO displayed the maximum level of $H_2S$ adsorption. But, the amount of adsorbed $H_2S$ decreased by 74% with an increase in the AC content from 7.5% to 30%. It was therefore considered that the adsorption efficiency was most optimized when the AC content was 7.5%.

Figure 23A:
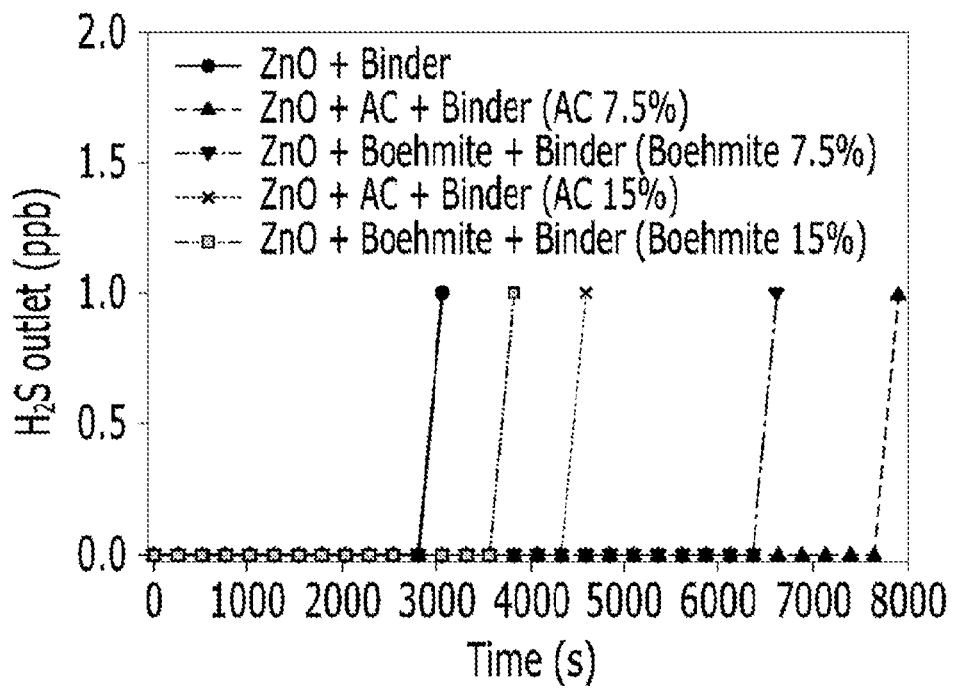
FIG. 23a, FIG. 23b and FIG. 23c present the results of performance evaluation of ZnO-boehmite composite adsorbents as a function of the contents of ZnO and boehmite in accordance with an embodiment of the present invention.
Figure 23B:
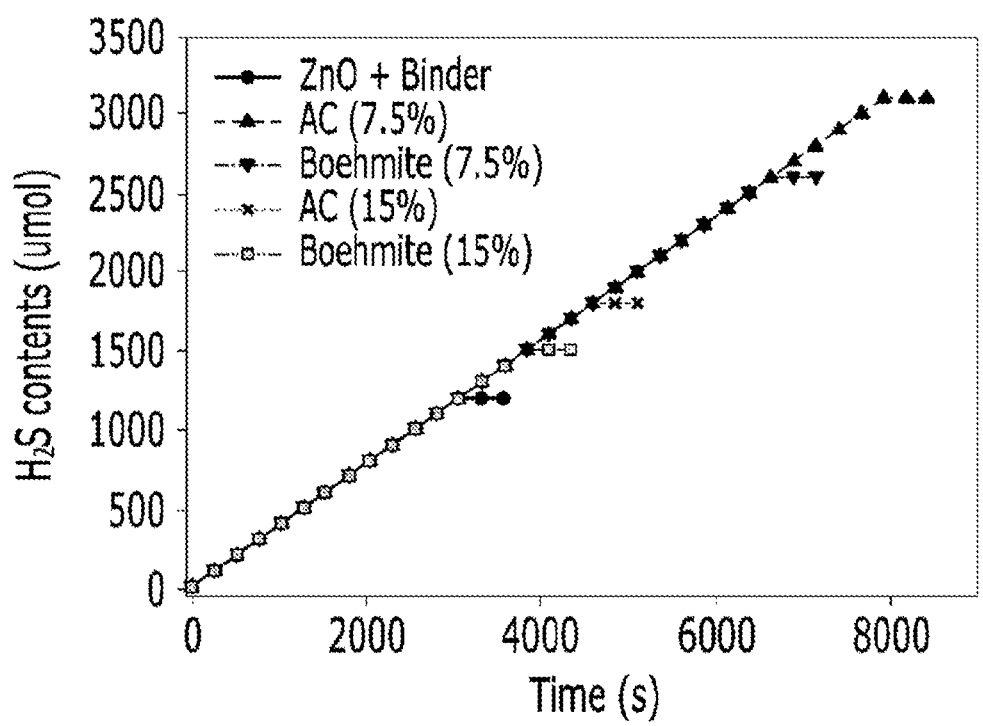
Figure 23C:
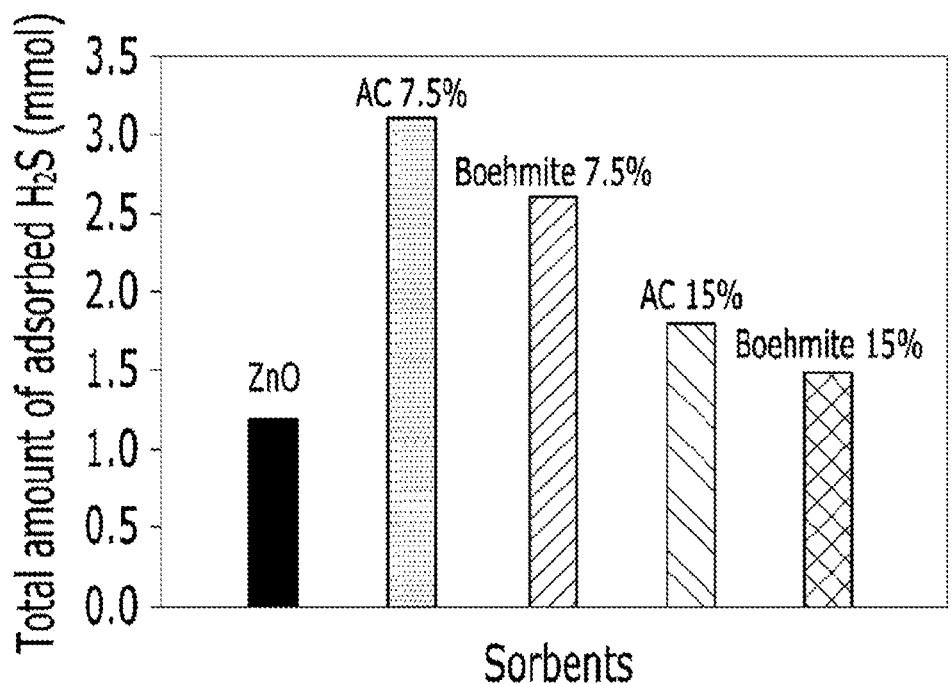

FIG. 23a, FIG. 23b and FIG. 23c are comparative graphs showing the $H_2S$ adsorption capacity as a function of the content of boehmite added to ZnO and the content of AC: (FIG. 23a) breakthrough curves; (FIG. 23b) the amount of adsorbed $H_2S$; and (FIG. 23c) a change in the amount of adsorbed $H_2S$. ZnO was mixed with 7.5% or 15% boehmite. Apart from this, for comparative evaluation, ZnO was mixed with AC of the same content of boehmite. Referring to FIG. 23a, the $H_2S$ breakthrough curves show that breakthrough time was 7,900 sec when the AC content was 7.5%, and 6,300 sec when the boehmite content was 7.5%. It was implied that AC contributed to the higher adsorption capacity than boehmite of the same content of AC. Further, referring to FIG. 23b and FIG. 23c, the addition of boehmite to ZnO led to the lower $H_2S$ adsorption capacity than that of boehmite of the same content to ZnO. In conclusion, for the ZnO adsorbents, the addition of AC was favored to $H_2S$ separation.

2-2. $Fe_2O_3$-Based Adsorbents

Figure 24A:
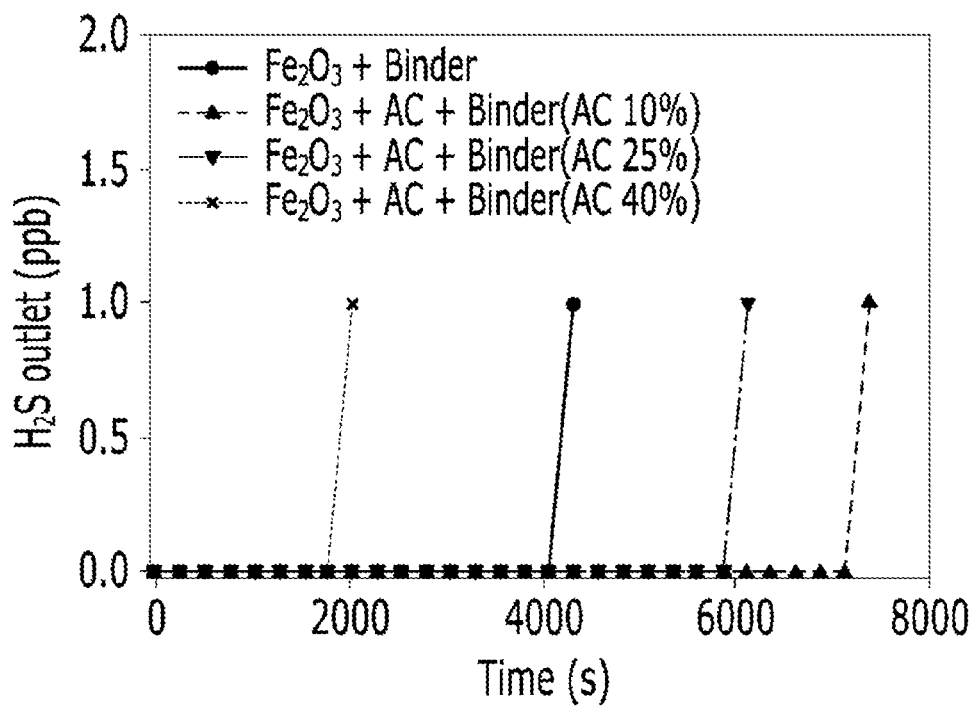
FIG. 24a and FIG. 24b present the results of performance evaluation of Fe₂O₃-AC composite adsorbents as a function of the contents of Fe₂O₃ and AC in accordance with an embodiment of the present invention.
Figure 24B:
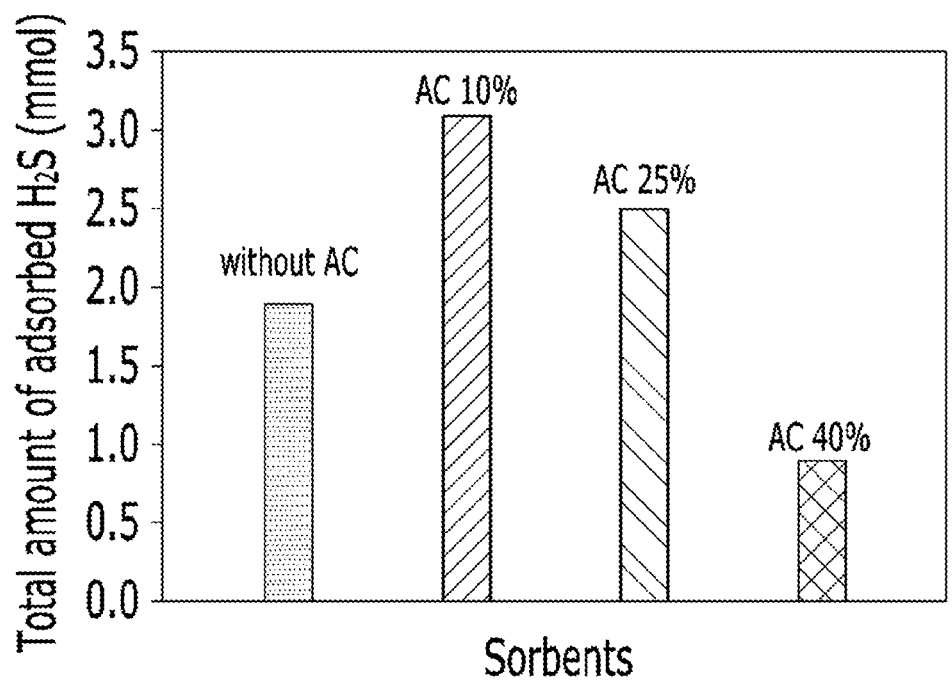

The $H_2S$ adsorbents containing $Fe_2O_3$ in combination with AC were measured in regards to the $H_2S$ adsorption capacity as a function of the AC content (10%, 25%, 40%). The measurement results are presented in FIG. 24a and FIG. 24b: (FIG. 24a) breakthrough curve; and (FIG. 24b) adsorption capacity. The AC content of 10% resulted in the highest adsorption capacity: the higher the AC content, the lower the adsorption capacity. The adsorbent with the AC content of 40% showed the lower adsorption capacity than the $Fe_2O_3$-only adsorbent. Such a deterioration of adsorption performance presumably resulted from the low reactivity to $H_2S$. The AC-free adsorbent had a $H_2S$ adsorption capacity of 1.9 mmol, whereas the adsorbent with the AC content of 10% had a higher $H_2S$ adsorption capacity up to 3.1 mmol. Yet, the $H_2S$ adsorption capacity declined with an increase in the AC content. For example, the $H_2S$ adsorption capacity of the adsorbent having an AC content of 40% was 0.9 mmol, which was lower by 72% than the adsorbent capacity of the adsorbent having an AC content of 10%.

2-3. Co—Zn-Based Adsorbents

Figure 25A:
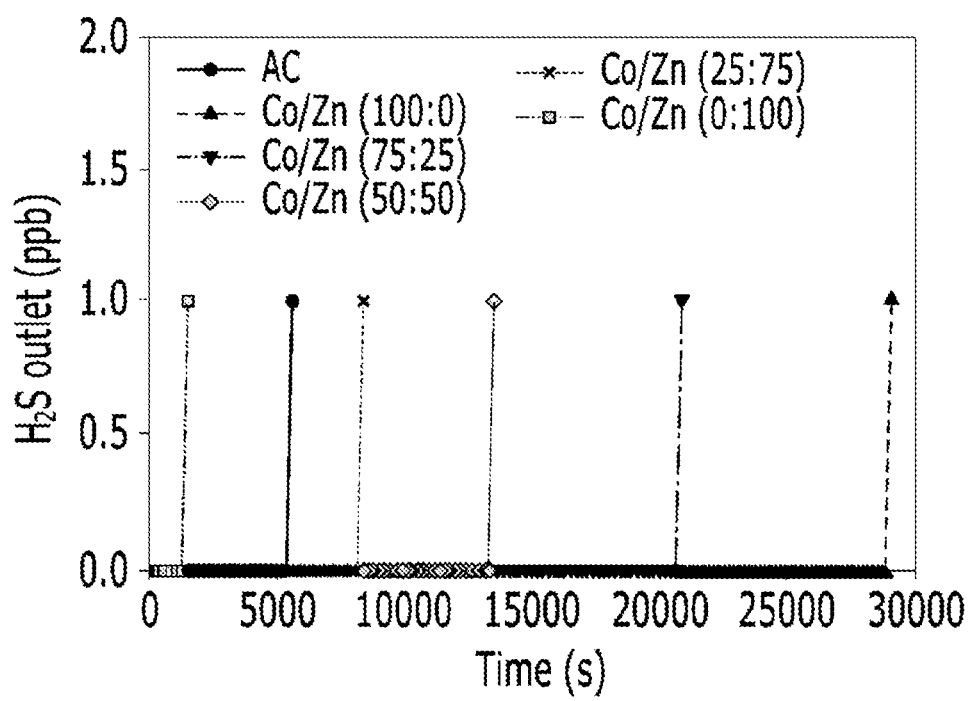
FIG. 25a and FIG. 25b present the results of performance evaluation of CoO—ZnO composite adsorbents in accordance with an embodiment of the present invention.
Figure 25B:
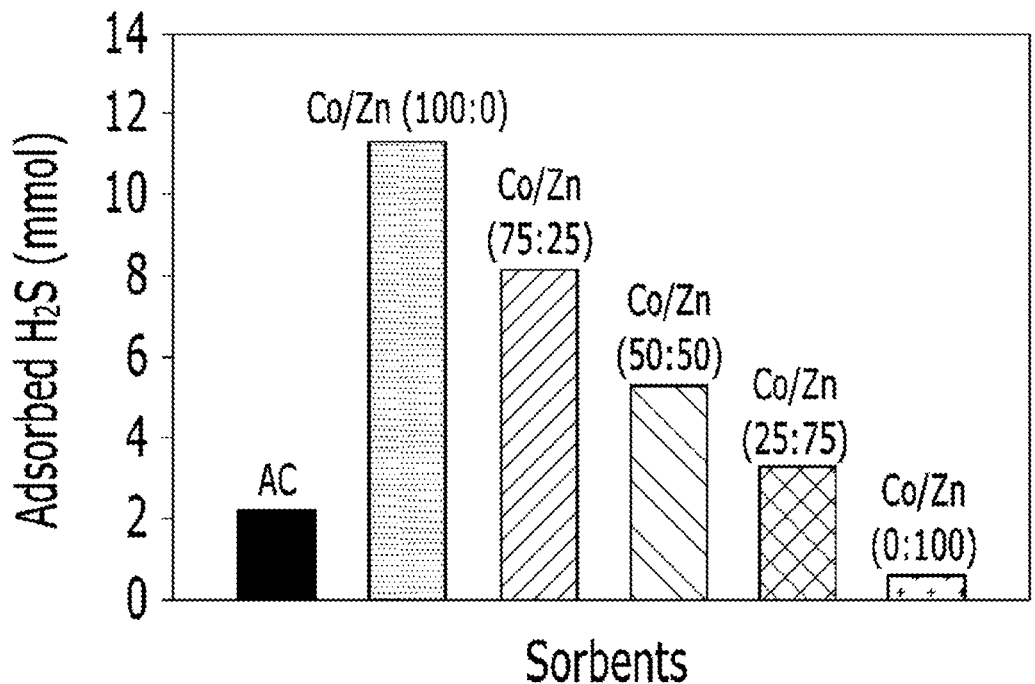

The $H_2S$ adsorbents containing metal oxides of CoO and ZnO according to the present invention were measured in regards to the $H_2S$ adsorption capacity. The measurement results are presented in FIG. 25a and FIG. 25b: (FIG. 25a) breakthrough curve; and (FIG. 25b) adsorption capacity. The adsorbent using CoO alone had the highest $H_2S$ removal efficiency, and the adsorbent using ZnO alone had the lowest $H_2S$ removal efficiency. The Co—Zn (100:0, 3 g) composite adsorbent showed a $H_2S$ adsorption capacity of 11.3 mmol, which was higher than the $H_2S$ adsorption capacity (2.2 mol) of the AC adsorbent. Yet, the higher the ZnO content, the lower the $H_2S$ adsorption capacity. In particular, the CoO adsorbent had a breakthrough time of 29,000 sec and showed a 3.67-fold higher $H_2S$ adsorption capacity than the Zn+AC adsorbent of which the breakthrough time was 7.900 sec. The $H_2S$ adsorption capacity of the ZnO adsorbent was 0.6 mmol, which was lower by 5.3% than the $H_2S$ adsorption capacity of the CoO adsorbent, 11.3 mmol. Therefore, the CoO-based adsorbents were considered as useful adsorbents for $H_2S$ separation.

2-4. CuO-Based Adsorbents

Figure 26A:
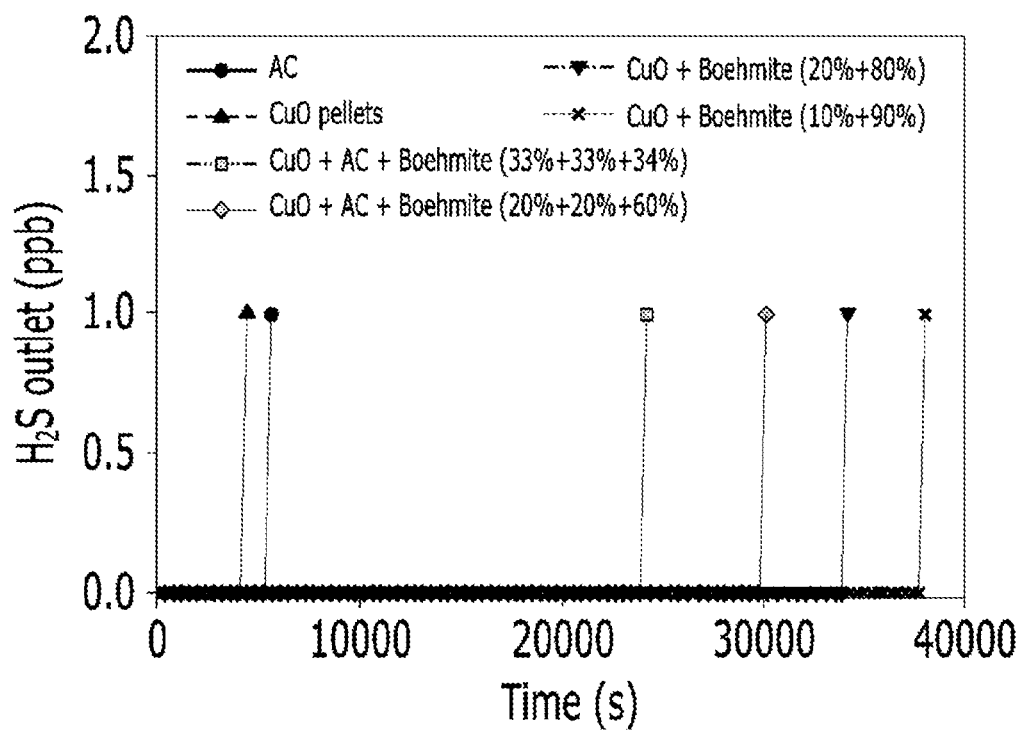
FIG. 26a, FIG. 26b and FIG. 26c present the results of performance evaluation of CuO-based composite adsorbents in accordance with an embodiment of the present invention.
Figure 26B:
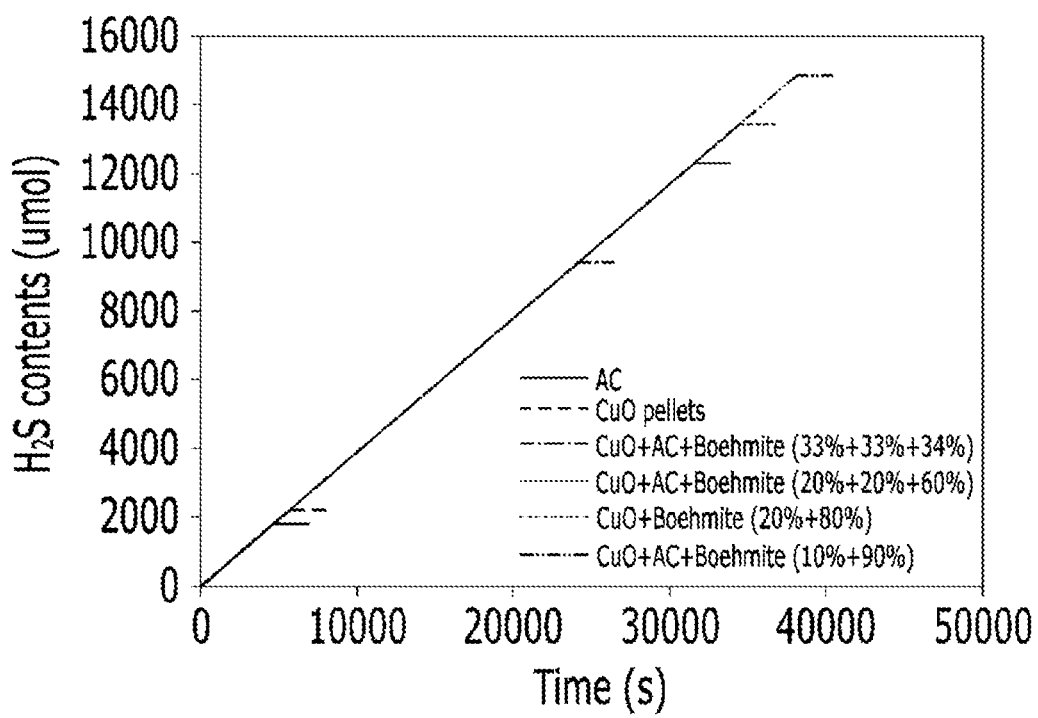
Figure 26C:
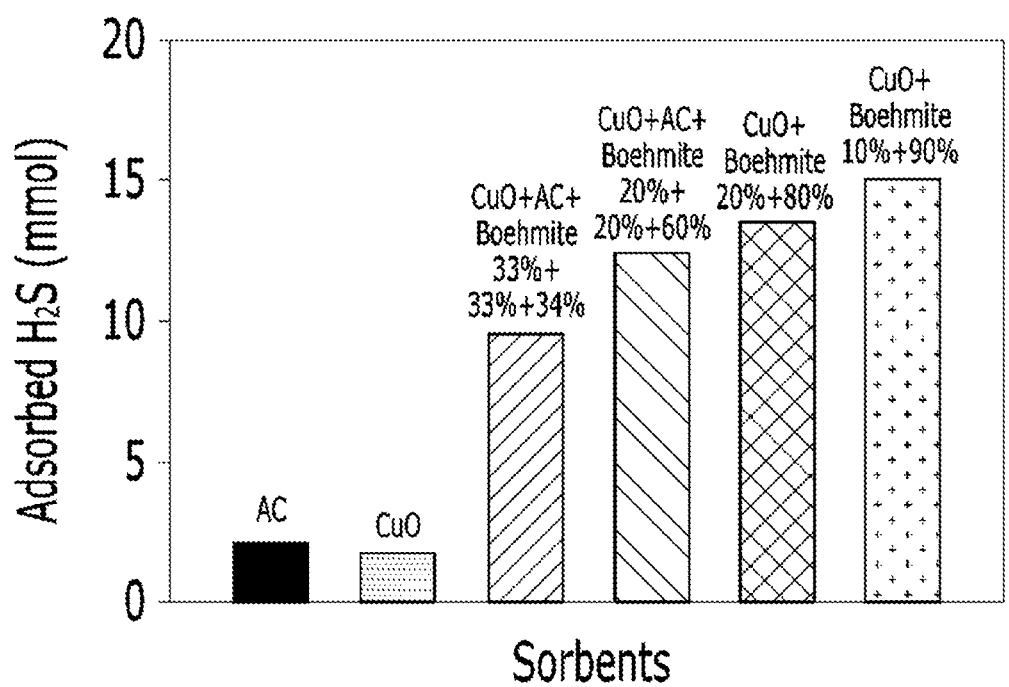

The $H_2S$ adsorbents of the present invention based on metal oxide of CuO were measured in regards to the $H_2S$ adsorption capacity. The measurement results are presented in the graph of FIG. 26a, FIG. 26b and FIG. 26c: (FIG. 26a) breakthrough curve; and (FIG. 26b) and (FIG. 26c) the amount of adsorbed $H_2S$. The pelleted CuO adsorbent using CuO alone had a low $H_2S$ adsorption capacity, which presumably resulted from the low specific surface area of the CuO adsorbent. As for the adsorbents using CuO in combination with an additive, the $H_2S$ adsorption capacity increased with a decrease in the CuO content, which was presumably due to the CuO well dispersed in the adsorbents. Particularly, the adsorbents with CuO 10%+boehmite had a higher $H_2S$ adsorption capacity than the CuO-only adsorbent by 733%, which was indicated by the breakthrough point of 38,000 sec in the breakthrough curve. The adsorbents using AC in combination with boehmite had a $H_2S$ adsorption capacity in the order of CuO:Boehmite (10:90) CuO:Boehmite (20:80) CuO:AC:Boehmite (20:20:60) CuO:AC:Boehmite (33:33:34).

2-5: Comparison/Evaluation of Adsorption Capacity of Pelleted $H_2S$ Adsorbents

Figure 27:
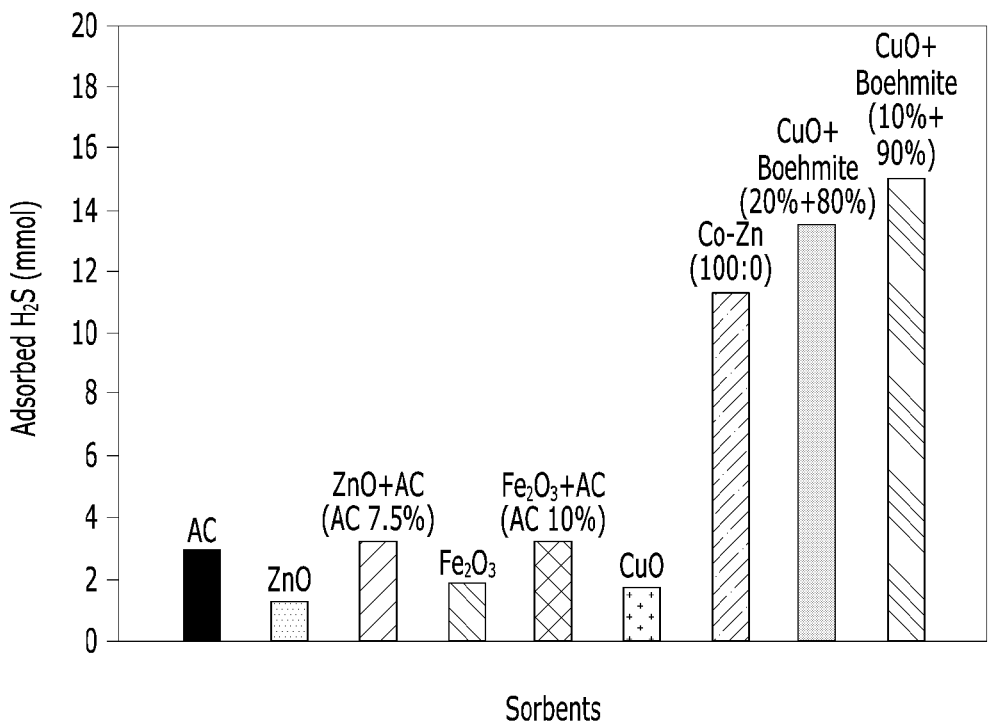
FIG. 27 presents the results of performance evaluation of all the adsorbents in regards to H₂S adsorption capacity in accordance with an embodiment of the present invention.

The results of comparative evaluation on the adsorption capacity of the afore-mentioned pelleted adsorbents are presented in FIG. 27. The adsorbents with CuO, Co—Zn, and CuO+boehmite in the adsorbent groups 2-3 and 2-4 displayed higher $H_2S$ adsorption capacity by 400 to 750% than those with AC, ZnO, Zn+AC, $Fe_2O_3$, and $Fe_2O_3$+AC in the adsorbent groups 2-1 and 2-2. The adsorbent using CuO alone had a low $H_2S$ adsorption capacity, but those using CuO in combination with boehmite or AC showed a considerably high $H_2S$ adsorption capacity. Particularly, the adsorbent with CuO (10%)+boehmite (90%) exhibited very excellent adsorption performance as shown by the $H_2S$ adsorption capacity of 15.8 mmol and the breakthrough point of 38,000 sec (10.5 hr) in its breakthrough curve. As a result, the adsorbents of the present invention were considered to be useful for high-grade $H_2S$ separation at low temperature (25° C.) and low concentration (100 ppm, $H_2S$).

2-6. CuO—ZnO—$Al_2O_3$-Based Adsorbents

Figure 28:
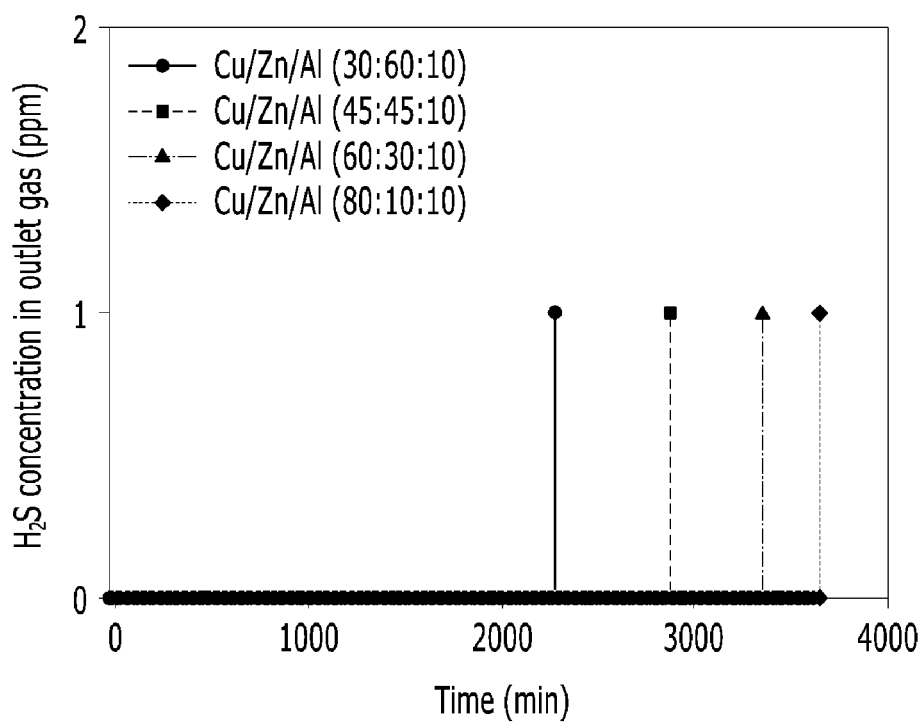
FIG. 28 presents the results of performance evaluation of Cu/Zn/Al-based composite adsorbents in accordance with an embodiment of the present invention (breakthrough curves).

The $H_2S$ adsorbents of the present invention based on a mixture of metal oxides of CuO, ZnO and $Al_2O_3$ were measured in regards to the $H_2S$ adsorption capacity. The measurement results are presented in FIG. 28. As can be seen from the breakthrough curves of FIG. 28, a complete adsorption of $H_2S$ was achieved for a defined period of time.

Figure 29:
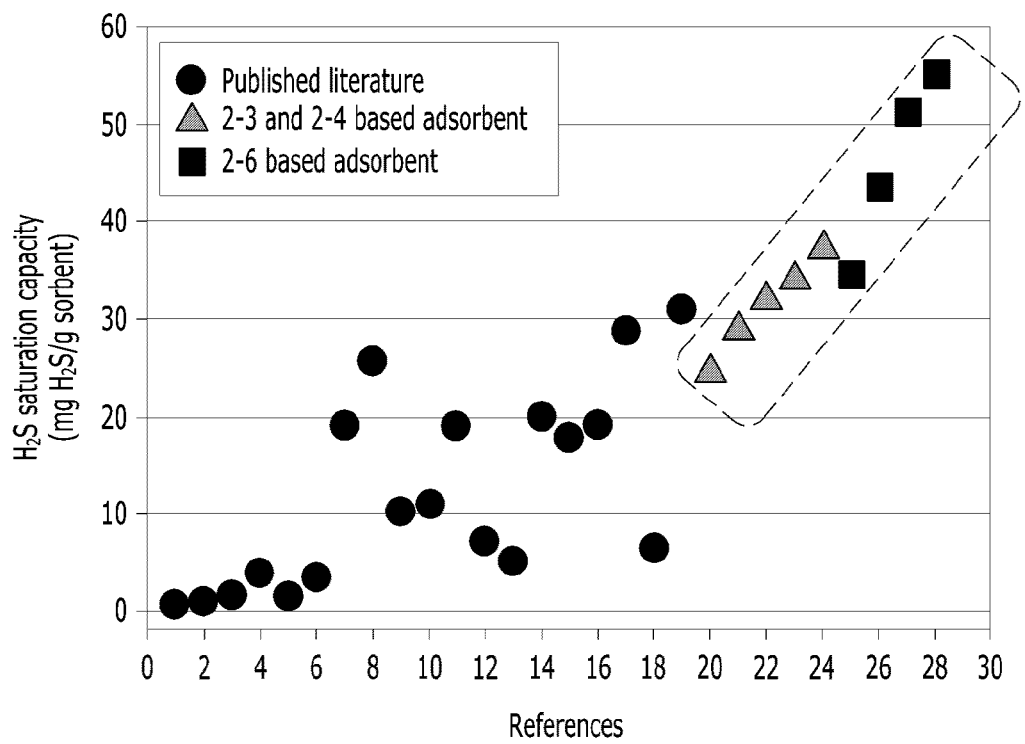
FIG. 29 presents the results of performance evaluation of Cu/Zn/Al-based composite adsorbents in accordance with an embodiment of the present invention.

In terms of the $H_2S$ adsorption capacity, the adsorbents of the groups 2-3 and 2-4 were compared with publicly known adsorbents. The results are presented in FIG. 29, and the compositions of the individual adsorbents are as given in Table 1. As can be seen from FIG. 29, the adsorbents prepared according to the embodiments of the present invention showed a high $H_2S$ adsorption capacity in relation to the publicly known adsorbents. In particular, the CuO—ZnO—$Al_2O_3$ mixture-based adsorbents had far higher adsorption capacity. Further, as for the CuO—ZnO—$Al_2O_3$ mixture-based adsorbents, the higher CuO content led to the higher $H_2S$ adsorption capacity ($H_2S$ adsorption capacity 55.3 mq($H_2S$)/q at CuO 80 wt %).

TABLE 1

| Ref. # | Adsorbent | $H_2S$ conc. (ppm) | Temp (° C.) | Reference |
|---|---|---|---|---|
| 1 | Z10/S16 | 800 | 25 | J. Hazard. Mat. 2016, 311, 142-150. |
| 2 | Z20/S16 | 800 | 25 | J. Hazard. Mat. 2016, 311, 142-150. |
| 3 | Z30/M48 | 800 | 25 | J. Hazard. Mat. 2016, 311, 142-150. |
| 4 | Z30/K6 | 800 | 25 | J. Hazard. Mat. 2016, 311, 142-150. |
| 5 | MnO2:AC (0.5:1) | 20 | 40 | Res. Chem. Intermed. 2015, 41, 6087-6104. |
| 6 | MnO2:AC (1:1) | 20 | 40 | Res. Chem. Intermed. 2015, 41, 6087-6104. |
| 7 | CuOZn1/AC | 3,000 | 30 | Chem. Eng. J. 2016, 304, 399-407. |

TABLE 1-continued

| Ref. # | Adsorbent | $H_2S$ conc. (ppm) | Temp (°C.) | Reference |
|---|---|---|---|---|
| 8 | Cu0.1Zn0.9/AC | 3000 | 30 | Chem. Eng. J. 2016, 304, 399-407. |
| 9 | ZnO/MCM-41 | 200 | 25 | Chem. Eng. J. 2012, 188, 222-232. |
| 10 | ZnO/KIT 6 | 200 | 25 | Chem. Eng. J. 2012, 188, 222-232. |
| 11 | ZnO/SiO2 | 8,000 | 30 | AIChE J. 2010, 56, 2898-2904. |
| 12 | CuO/SiO2-MSU-1 | 50,000 | 25 | Microp. Mesop. Mater. 2013, 168, 111-120. |
| 13 | ZnO/SiO2-MSU-1 | 50,000 | 25 | Microp. Mesop. Mater. 2013, 168, 111-120. |
| 14 | KOH/AC | 200 | 30 | Int. J. Hyd. Energy. 2014, 39, 21753-21766. |
| 15 | $TiO_2$/zeolite | 1,000 | 40 | Fuel, 2015, 157, 183-190. |
| 16 | ZnO (commercial) | 10,000 | 20 | Ind. Eng. Chem. Res. 2010, 49, 8388-8396. |
| 17 | 5 wt. % Mn/$\gamma$-$Al_2O_3$ | 10,000 | 500 | Chemosphere. 2005, 58, 467-474. |
| 18 | 5 wt. % Zn/$\gamma$-$Al_2O_3$ | 10,000 | 700 | Chemosphere. 2005, 58, 467-474. |
| 19 | Cu—Mn—O | 10,000 | 627 | Ind. Eng. Chem. Res. 2005, 44,5221-5226. |
| 20 | CoO (synthesized) | 100 | 25 | Example of invention |
| 21 | CuO-Boehmite (20/80) | 100 | 25 | Example of invention |
| 22 | CuO-Boehmite (10/90) | 100 | 25 | Example of invention |
| 23 | CuO-Boehmite (8/92) | 100 | 25 | Example of invention |
| 24 | CuO (synthesized) | 100 | 25 | Example of invention |
| 25 | Cu—Zn—Al (Cu: 30 wt %) | 100 | 25 | Example of invention |
| 26 | Cu—Zn—Al (Cu: 45 wt %) | 100 | 25 | Example of invention |
| 27 | Cu—Zn—Al (Cu: 60 wt %) | 100 | 25 | Example of invention |
| 28 | Cu—Zn—Al (Cu: 80 wt %) | 100 | 25 | Example of invention |

2-7. Economic Analysis of $H_2S$ Adsorbents

Figure 30:
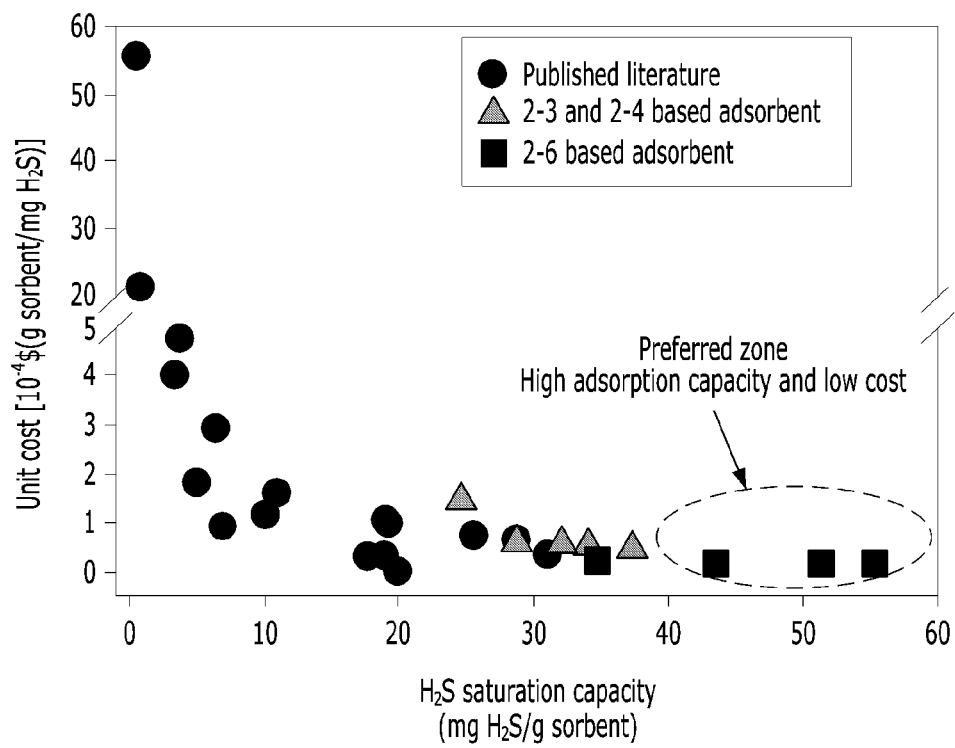
FIG. 30 is a graph showing the economic analysis of the publicly known adsorbents and the novel adsorbents in accordance with an embodiment of the present invention.

An economic analysis of the adsorbents of the present invention and the publicly known adsorbents as listed in Table 1 was carried out, and the results are presented in FIG. 30. As can be seen from FIG. 30, the adsorbents of the present invention exhibited higher economic feasibility in the aspect of cost than the publicly known adsorbents. That is, the adsorbents of the present invention were superior to the publicly known adsorbents in the $H_2S$ adsorption capacity and the economic feasibility as well and hence considered to be more usefully available as $H_2S$ adsorbents.

Example 3: Analysis of Absorption/Adsorption Process for $H_2S$ Separation 3-1. Analysis of Absorption Process According to an ASPEN simulation with the absorbents of Example 1, the absorption process resulted in removing 99.99% of $H_2S$ (conc. 100 ppm) in biogas and reducing the $H_2S$ concentration to 10 ppm (Refer to FIG. 31).

In a case-specific simulation of $H_2S$ separation for purification of a biogas, as given in Table 2, MDEA+PZ had an L/G ratio of 6.13; whereas MDEA+APA had a lower L/G ratio of 5.73, which accounted for a higher process efficiency.

TABLE 2

| Case 1: | Case 2: |
|---|---|
| Key features: | Key features: |
| Solvent: alpha-MDEA (MEDA 40%, PZ 5%) | Solvent: MEDA 40% – APA 5% |
| Target: 10 ppb $H_2S$ in outgas | Target: 10 ppb $H_2S$ in outgas |
| L/G ratio: 6.13 | L/G ratio: 5.73 |

The absorbents of the present invention had a higher $H_2S$ separation efficiency than the conventional absorbents for removal of $H_2S$ from a biogas. This implicitly shows that the absorbents of the present invention can be used as a biogas purification technology for producing the final product, clean energy fuels.

3-2. Analysis of Adsorption Process $H_2S$ breakthrough curves were used to calculate the size of the adsorbents and the process adopted in the removal of $H_2S$ from the biogas in a fixed-bed reactor with adsorbents of Example 2 of the present invention. Size calculation was conducted separately for two of the adsorbents exploited in the analysis of the adsorption process: the $ZnO_+AC$ adsorbent (breakthrough time: 2.2 hr) in case I and the CuO+ boehmite adsorbent (breakthrough time: 10.5 hr) in case II. The amount of the consumed adsorbents and the size of the $H_2S$ adsorption process in a two-step demonstration process were calculated based on the biogas produced from anaerobic fermentation of food waste (150 kg food waste/day). The results are presented in FIG. 25a and FIG. 25b. The adsorbent of case II (CuO+boehmite), most excellent in performance among the exploited adsorbents, was consumed at a rate of 71.42 g adsorbent/day in reducing the $H_2S$ concentration of the biogas from 100 ppm to 100 ppb. This daily consumption of the adsorbent acquired in the demonstration process corresponds to an annual consumption of 25.7 kg and 53.5 L (bulk density: 0.48 g/cm3) in volume. In conclusion, the $H_2S$ adsorbents of the present invention are capable of eliminating $H_2S$ to reduce a low $H_2S$ concentration of 100 ppm to 10 ppb or below at low temperature (25° C.) for $H_2S$ removal from a biogas and hence considered as an efficient biogas purification technology for producing the final products, clean energy fuels, through a small and medium-scale process.

10 FIRST BIOGAS PURIFIER
20 SECOND BIOGAS PURIFIER
30 REFORMER
101 ABSORPTION TOWER
102 REGENERATION TOWER
103 REBOILER
201 ADSORPTION TOWER

What is claimed is:

1. An absorbent for absorption of an acid gas in a biogas, comprising:
 a tertiary amine represented by the following [Chemical Formula] 1;
 a primary or secondary amine; and
 a solvent;
 wherein the primary or secondary amine comprises any one amine selected from the group consisting of AMP (2-amino-2-methyl-1-propanol), APA(bis(3-aminopropyl)amine), DAB(1,4-diaminobutane), DBA (dibutylamine), AB(2-amino-1-butanol), AP(5-amino-1-pentanol), PED(N-propylethylenediamine), DEP(1-dimethylamino-2-propanol), PA(1-propanamine), DPA (N-propyl-propanamine), BA(1-butanamine), IBA(2-methyl-1-propanamine), SBA(2-butanamine), 1,2-dimethylpropylamine, 3-methyl-2-butanamine, hexylamine, allylamine, diallylamine, 3-methoxy propylamine, 3-ethoxyl propylamine, 3-propoxypropylamine, 3-isopropoxy propylamine, 3-butoxyl propylamine, 3-decyloxypropylamine, 3-lauryloxy propylamine, dimethylamino ethylamine, ethylaminoethylamine, 1,2-diaminopropane, 1,3-diamino propane, N,N-diethyl-1,3-propanediamine, dibutylamino propylamine, bis-(3-aminopropyl) ether, 1,2-diaminobutane, 1,4-diaminobutane, and combinations thereof;
wherein the primary or secondary amine does not include piperazine;
wherein the content of the primary or secondary amine is 8 to 15 parts by weight with respect to 100 parts by weight of the tertiary amine;
wherein [Chemical Formula 1] is:

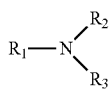

wherein $R_1$ is linear $C_1$-$C_3$ alkyl or linear $C_2$-$C_5$ alkenyl; and
wherein $R_2$ and $R_3$ are independently linear $C_1$-$C_5$ alkyl having a terminal thereof substituted with a hydroxyl group, or linear $C_2$-$C_5$ alkenyl having a terminal thereof substituted with a hydroxyl group.

2. The absorbent as claimed in claim 1, wherein in [Chemical Formula] 1,
$R_1$ is linear $C_1$-$C_3$ alkyl; and
$R_2$ and $R_3$ are independently linear $C_1$-$C_5$ alkyl having a terminal thereof substituted with a hydroxyl group.

3. The absorbent as claimed in claim 1, wherein the tertiary amine represented by [Chemical Formula] 1 is methyl diethanolamine (MDEA).

4. The absorbent as claimed in claim 1, wherein the content of the tertiary amine is 1 to 85 parts by weight with respect to 100 parts by weight of the absorbent.

5. The absorbent as claimed in claim 1, wherein the biogas comprises 20 to 50 vol % of methane ($CH_4$), 5 to 30 vol % of carbon dioxide ($CO_2$), and 5 to 30,000 ppm of hydrogen sulfide ($H_2S$).

6. The absorbent as claimed in claim 1, wherein the acid gas comprises a gas selected from the group consisting of carbon dioxide ($CO_2$), hydrogen sulfide ($H_2S$), sulfur dioxide ($SO_2$), sulfur trioxide ($SO_3$), carbonyl sulfide (COS), carbon disulfide ($CS_2$), mercaptan (RSH), and combinations thereof.

* * * * *